(12) United States Patent
Yuki et al.

(10) Patent No.: US 11,530,254 B2
(45) Date of Patent: Dec. 20, 2022

(54) NOROVIRUS ANTIBODY

(71) Applicant: The University of Tokyo, Tokyo (JP)

(72) Inventors: Yoshikazu Yuki, Tokyo (JP); Hiroshi Kiyono, Tokyo (JP); Shiho Kurokawa, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 610 days.

(21) Appl. No.: 16/498,824

(22) PCT Filed: Mar. 30, 2018

(86) PCT No.: PCT/JP2018/013543
§ 371 (c)(1),
(2) Date: Sep. 27, 2019

(87) PCT Pub. No.: WO2018/181866
PCT Pub. Date: Oct. 4, 2018

(65) Prior Publication Data
US 2021/0087258 A1 Mar. 25, 2021

(30) Foreign Application Priority Data
Mar. 31, 2017 (JP) .............................. JP2017-070757

(51) Int. Cl.
C07K 16/10 (2006.01)
C12N 15/82 (2006.01)
(Continued)

(52) U.S. Cl.
CPC ............ C07K 16/10 (2013.01); A61K 39/395 (2013.01); A61P 31/14 (2018.01); C12N 15/8258 (2013.01); *A61K 2039/552* (2013.01)

(58) Field of Classification Search
None
See application file for complete search history.

(56) References Cited

U.S. PATENT DOCUMENTS

| 10,000,556 | B2 * | 6/2018 | Bok | .................. A61P 31/14 |
| 2008/0107601 | A1 * | 5/2008 | Lauwereys | ............ C07K 16/28 |
| | | | | 435/7.1 |
| 2021/0087258 | A1 * | 3/2021 | Yuki | .................... C12N 5/0679 |

FOREIGN PATENT DOCUMENTS

| JP | 2015-171363 A | 10/2015 |
| WO | 2010/017542 A1 | 2/2010 |

(Continued)

OTHER PUBLICATIONS

Instant SEQ ID No. 1 alignment with SEQ ID No. 1 of 10054598 Jul. 2010.*

(Continued)

*Primary Examiner* — Shanon A. Foley
(74) *Attorney, Agent, or Firm* — Wenderoth, Link & Ponack, LLP

(57) ABSTRACT

An antibody is provided that inhibits infection of cells with a norovirus. The antibody is a nanoantibody comprising a polypeptide described in (a), (b), or (c), and inhibiting infection of intestinal cells with HuNoV GII.4: (a) a polypeptide consisting of the amino acid sequence of SEQ ID NO: 1, SEQ ID NO: 5, SEQ ID NO: 9, or SEQ ID NO: 13; (b) a polypeptide consisting of an amino acid sequence comprising a substitution, deletion, insertion and/or addition of one or several amino acids with respect to the amino acid sequence of SEQ ID NO: 1, SEQ ID NO: 5, SEQ ID NO: 9, or SEQ ID NO: 13; and (c) a polypeptide consisting of an amino acid sequence having a sequence identity of 80% or more to the amino acid sequence of SEQ ID NO: 1, SEQ ID NO: 5, SEQ ID NO: 9, or SEQ ID NO: 13.

23 Claims, 12 Drawing Sheets

Specification includes a Sequence Listing.

(51) Int. Cl.
    A61K 39/395    (2006.01)
    A61P 31/14     (2006.01)
    A61K 39/00     (2006.01)

(56) References Cited

FOREIGN PATENT DOCUMENTS

| WO | 2012/011396 A1 | 1/2012 |
|---|---|---|
| WO | 2014/126921 | 8/2014 |
| WO | 2014/183052 A1 | 11/2014 |
| WO | WO 2014183052 * | 11/2014 |
| WO | 2016/059113 | 4/2016 |
| WO | 2016/059113 A1 | 4/2016 |
| WO | 2017/011394 | 1/2017 |

OTHER PUBLICATIONS

Instant SEQ ID No. 5 alignment with SEQ ID No. 3266 of USPgPub 20200165630 Apr. 2016.*
Instant SEQ ID No. 5 alignment with SEQ ID No. 12 of 10000556 May 2013.*
Garaicoechea et al. (PLoS One. 2015; 10 (8): e0133665).*
Office Action dated Mar. 15, 2021 in corresponding Taiwan Patent Application No. 107111095, with English Translation, 14 pages.
Garaicoechea, Lorena et al., "Llama Nanoantibodies with Therapeutic Potential against Human Norovirus Diarrhea", PLOS One, Aug. 12, 2015, vol. 10, No. 8, 33 pages; Cited in ISR dated Jul. 3, 2018.
Koromyslova, Anna D. et al., "Nanobody Binding to a Conserved Epitope Promotes Norovirus Particle Disassembly", Journal of Virology, Mar. 2015, vol. 89, No. 5, pp. 2718-2730; Cited in ISR dated Jul. 3, 2018.
Glass, Roger I. et al., "Norovirus Gastroenteritis", NIH Public Access, N Engl J Med., Oct. 29, 2009, 17 pages Cited in the Specification.
Hamers-Casterman, C et al., "Naturally occurring antibodies devoid of light chains", Nature Publishing Group, vol. 363, Jun. 3, 1993, pp. 446-448; Cited in the Specification.
Notice of Reasons for Rejection dated Dec. 1, 2020 in Japanese Patent Application No. 2019-510223, with English Translation.
Extended European Search Report dated Nov. 24, 2020 in corresponding European Patent Application No. 18775369.4.
Lindesmith et al., "Broad Blockade Antibody Responses in Human Volunteers after Immunization with a Multivalent Norovims VLP Candidate Vaccine: Immunological Analyses from a Phase I Clinical Trial", PLOS Medicine, 2015, vol. 12, No. 3, pp. 1-32.
Lochridge et al., "Epitopes in the P2 domain of norovirus VP1 recognized by monoclonal antibodies that block cell interactions", Journal of General Virology, 2005, vol. 86, pp. 2799-2806.
Ettayebi et al., "Recombinant norovirus-specific scFv inhibit virus-like particle binding to cellular ligands", Virology Journal, 2008, vol. 5, No. 1, pp. 1-8.
Shanker et al., "Structural basis for norovirus neutralization by an HBGA blocking human IgA antibody", Proceedings of the National Academy of Sciences, 2016, vol. 113, No. 40, pp. E5830-E5837.
Hansman et al., "Structural Basis for Broad Detection of Genogroup II Noroviruses by a Monoclonal Antibody That Binds to a Site Occluded in the Viral Particle", Journal of Virology, 2012, vol. 86, No. 7, pp. 3635-3646.
Allen et al., "Characterisation of a GII-4 norovirus variant-specific surface-exposed site involved in antibody binding", Virology Journal, 2009, vol. 6, No. 1, pp. 1-11.
Lindesmith et al., "Particle Conformation Regulates Antibody Access to a Conserved GII.4 Norovirus Blockade Epitope", Journal of Virology, 2014, vol. 88, No. 16, pp. 8826-8842.
Li et al., "Identification and characterization of a native epitope common to norovirus strains GII4, GII/7 and GII/8". Virus Research, 2009, vol. 140, pp. 188-193.
Steeland et al., "Nanobodies as therapeutics: big opportunities for small antibodies", Drug Discovery Today, 2016, vol. 21, No. 7, pp. 1076-1113.

* cited by examiner

SEQUENCE LISTING

```
<160> NUMBER OF SEQ ID NOS: 30

<210> SEQ ID NO 1
<211> LENGTH: 120
<212> TYPE: PRT
<213> ORGANISM: Lama glama

<400> SEQUENCE: 1

Glu Val Gln Leu Val Glu Ser Gly Gly Gly Leu Val Gln Ala Gly Gly
1               5                   10                  15

Ser Leu Arg Leu Ser Cys Leu Ala Ser Gly Ser Ile Ser Ser Ile Asn
            20                  25                  30

Thr Met Ala Trp Tyr Arg Gln Ala Pro Gly Lys Gln Arg Glu Leu Val
        35                  40                  45

Ala Ser Ile Ser Gly Gly Gly Thr Asn Tyr Ala Asp Ser Val Lys
    50                  55                  60

Gly Arg Phe Thr Ile Ser Thr Asp Asn Ala Lys Asn Thr Val Tyr Leu
65                  70                  75                  80

Gln Met Asn Ser Leu Glu Ser Glu Asp Thr Ala Val Tyr Phe Cys Asn
                85                  90                  95

Leu His Asn Phe Ser Pro Ile Ser Pro Pro Arg Ser Tyr Trp Gly Gln
            100                 105                 110

Gly Thr Gln Val Thr Val Ser Ser
        115                 120

<210> SEQ ID NO 2
<211> LENGTH: 360
<212> TYPE: DNA
<213> ORGANISM: Lama glama

<400> SEQUENCE: 2
gaagttcaat tagttgaatc tggtggtggt ttagttcaag ctggtggttc tttacgttta        60
tcttgtttag cttctggttc tatttcttct attaatacta tggcttggta tcgtcaagct       120
cctggtaaac aacgtgaatt agttgcttct atttcttctg gtggtggtac taattatgct       180
gattctgtta aaggtcgttt tactatttct actgataatg ctaaaaatac tgtttattta       240
caaatgaatt ctttagaatc tgaagatact gctgtttatt tttgtaattt acataatttt       300
tctcctattt ctcctcctcg ttcttattgg ggtcaaggta ctcaagttac tgtttcttct       360

<210> SEQ ID NO 3
<211> LENGTH: 143
<212> TYPE: PRT
<213> ORGANISM: Lama glama

<400> SEQUENCE: 3

Glu Val Gln Leu Val Glu Ser Gly Gly Gly Leu Val Gln Ala Gly Gly
1               5                   10                  15

Ser Leu Arg Leu Ser Cys Leu Ala Ser Gly Ser Ile Ser Ser Ile Asn
            20                  25                  30
```

Thr Met Ala Trp Tyr Arg Gln Ala Pro Gly Lys Gln Arg Glu Leu Val
            35                  40                  45

Ala Ser Ile Ser Ser Gly Gly Thr Asn Tyr Ala Asp Ser Val Lys
        50                  55                  60

Gly Arg Phe Thr Ile Ser Thr Asp Asn Ala Lys Asn Thr Val Tyr Leu
65                  70                  75                  80

Gln Met Asn Ser Leu Glu Ser Glu Asp Thr Ala Val Tyr Phe Cys Asn
                85                  90                  95

Leu His Asn Phe Ser Pro Ile Ser Pro Pro Arg Ser Tyr Trp Gly Gln
                100                 105                 110

Gly Thr Gln Val Thr Val Ser Ser Ala Ala Ala Asp Tyr Lys Asp Asp
                115                 120                 125

Asp Asp Lys Gly Ala Ala His His His His His His Gly Ala Ala
130                 135                 140

<210> SEQ ID NO 4
<211> LENGTH: 429
<212> TYPE: DNA
<213> ORGANISM: Lama glama

<400> SEQUENCE: 4
gaagttcaat tagttgaatc tggtggtggt ttagttcaag ctggtggttc tttacgttta      60
tcttgtttag cttctggttc tatttcttct attaatacta tggcttggta tcgtcaagct     120
cctggtaaac aacgtgaatt agttgcttct atttcttctg gtggtggtac taattatgct     180
gattctgtta aaggtcgttt tactatttct actgataatg ctaaaaatac tgtttattta     240
caaatgaatt ctttagaatc tgaagatact gctgtttatt tttgtaattt acataatttt     300
tctcctattt ctcctcctcg ttcttattgg ggtcaaggta ctcaagttac tgtttcttct     360
gctgctgctg attataaaga tgatgatgat aaaggtgctg ctcatcatca tcatcatcat     420
ggtgctgct                                                             429

<210> SEQ ID NO 5
<211> LENGTH: 120
<212> TYPE: PRT
<213> ORGANISM: Lama glama

<400> SEQUENCE: 5

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ser Ile Asn
            20                  25                  30

Gly Val Ala Trp Tyr Arg Gln Ala Pro Gly Lys Gln Arg Glu Leu Val
            35                  40                  45

Gly Gly Ile Ser Arg Ser Gly Trp Thr Asn Tyr Ala Asp Ser Val Lys
        50                  55                  60

Gly Arg Phe Thr Ile Ser Ser Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Asn Leu His Ser Gly Leu Gly Asn Val Lys Asn Tyr Trp Gly Gln
                100                 105                 110

Gly Thr Gln Val Thr Val Ser Ser
                115                 120

```
<210> SEQ ID NO 6
<211> LENGTH: 360
<212> TYPE: DNA
<213> ORGANISM: Lama glama

<400> SEQUENCE: 6
gaagttcaat tagttgaatc tggtggtggt ttagttcaag ctggtggttc tttacgttta      60
tcttgtgctg cttctggttc tacttttttct attaatggtg ttgcttggta tcgtcaagct     120
cctggtaaac aacgtgaatt agttggtggt atttctcgtt ctggttggac taattatgct     180
gattctgtta aggtcgtttt tactatttct tctgataatg ctaaaaatac tgtttattta     240
caaatgaatt ctttaaaacc tgaagatact gctgtttatt attgtaatgt taatttacat     300
tctggtttag gtaatgttaa aaattattgg ggtcaaggta ctcaagttac tgtttcttct     360

<210> SEQ ID NO 7
<211> LENGTH: 143
<212> TYPE: PRT
<213> ORGANISM: Lama glama

<400> SEQUENCE: 7

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ser Ile Asn
            20                  25                  30

Gly Val Ala Trp Tyr Arg Gln Ala Pro Gly Lys Gln Arg Glu Leu Val
        35                  40                  45

Gly Gly Ile Ser Arg Ser Gly Trp Thr Asn Tyr Ala Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Asn Leu His Ser Gly Leu Gly Asn Val Lys Asn Tyr Trp Gly Gln
            100                 105                 110

Gly Thr Gln Val Thr Val Ser Ser Ala Ala Ala Asp Tyr Lys Asp Asp
        115                 120                 125

Asp Asp Lys Gly Ala Ala His His His His His His Gly Ala Ala
    130                 135                 140

<210> SEQ ID NO 8
<211> LENGTH: 429
<212> TYPE: DNA
<213> ORGANISM: Lama glama

<400> SEQUENCE: 8
gaagttcaat tagttgaatc tggtggtggt ttagttcaag ctggtggttc tttacgttta      60
tcttgtgctg cttctggttc tacttttttct attaatggtg ttgcttggta tcgtcaagct     120
cctggtaaac aacgtgaatt agttggtggt atttctcgtt ctggttggac taattatgct     180
gattctgtta aggtcgtttt tactatttct tctgataatg ctaaaaatac tgtttattta     240
caaatgaatt ctttaaaacc tgaagatact gctgtttatt attgtaatgt taatttacat     300
tctggtttag gtaatgttaa aaattattgg ggtcaaggta ctcaagttac tgtttcttct     360
gctgctgctg attataaaga tgatgatgat aaaggtgctg ctcatcatca tcatcatcat     420
ggtgctgct                                                             429
```

<210> SEQ ID NO 9
<211> LENGTH: 117
<212> TYPE: PRT
<213> ORGANISM: Lama glama

<400> SEQUENCE: 9

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Pro Asn
            20                  25                  30

Val Met Gly Trp Tyr Arg Gln Ala Pro Gly Lys Gln Arg Glu Leu Val
        35                  40                  45

Ala Ser Lys Thr Ser Gly Arg Leu Ser Asn Tyr Ala Asp Ser Val Lys
    50                  55                  60

Gly Arg Phe Ala Ile Ser Arg Asp Phe Ala Lys Asn Thr Leu Tyr Leu
65                  70                  75                  80

Gln Met Asn Asn Leu Arg Pro Asp Asp Thr Ala Val Tyr Tyr Cys Arg
                85                  90                  95

Leu Trp Asp Ser Ala Arg Ser Thr Glu Tyr Trp Gly Gln Gly Thr Gln
            100                 105                 110

Val Thr Val Ser Ser
        115

<210> SEQ ID NO 10
<211> LENGTH: 351
<212> TYPE: DNA
<213> ORGANISM: Lama glama

<400> SEQUENCE: 10
gaagttcaat tagttgaatc tggtggtggt ttagttcaag ctggtggttc tttacgttta      60
tcttgtgctg cttctggtcg tacttttggt cctaatgtta tgggttggta tcgtcaagct     120
cctggtaaac aacgtgaatt agttgcttct aaaacttctg gtcgtttatc taattatgct     180
gattctgtta aaggtcgttt tgctatttct cgtgattttg ctaaaaatac tttatattta     240
caaatgaata atttacgtcc tgatgatact gctgtttatt attgtcgttt atgggattct     300
gctcgttcta ctgaatattg gggtcaaggt actcaagtta ctgtttcttc t              351

<210> SEQ ID NO 11
<211> LENGTH: 140
<212> TYPE: PRT
<213> ORGANISM: Lama glama

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Pro Asn
            20                  25                  30

Val Met Gly Trp Tyr Arg Gln Ala Pro Gly Lys Gln Arg Glu Leu Val
        35                  40                  45

Ala Ser Lys Thr Ser Gly Arg Leu Ser Asn Tyr Ala Asp Ser Val Lys
    50                  55                  60

Gly Arg Phe Ala Ile Ser Arg Asp Phe Ala Lys Asn Thr Leu Tyr Leu
65                  70                  75                  80

Gln Met Asn Asn Leu Arg Pro Asp Asp Thr Ala Val Tyr Tyr Cys Arg
                85                  90                  95

Leu Trp Asp Ser Ala Arg Ser Thr Glu Tyr Trp Gly Gln Gly Thr Gln
            100                 105                 110

Val Thr Val Ser Ser Ala Ala Ala Asp Tyr Lys Asp Asp Asp Lys
         115                 120                 125

Gly Ala Ala His His His His His Gly Ala Ala
         130                 135                 140

<210> SEQ ID NO 12
<211> LENGTH: 420
<212> TYPE: DNA
<213> ORGANISM: Lama glama

<400> SEQUENCE: 12
gaagttcaat tagttgaatc tggtggtggt ttagttcaag ctggtggttc tttacgttta    60
tcttgtgctg cttctggtcg tactttggg cctaatgtta tgggttggta tcgtcaagct   120
cctggtaaac aacgtgaatt agttgcttct aaaacttctg gtcgtttatc taattatgct   180
gattctgtta aggtcgtttt gctatttct cgtgattttg ctaaaaatac tttatattta   240
caaatgaata atttacgtcc tgatgatact gctgtttatt attgtcgttt atgggattct   300
gctcgttcta ctgaatattg ggtcaaggt actcaagtta ctgtttcttc tgctgctgct   360
gattataaag atgatgatga taaaggtgct gctcatcatc atcatcatca tggtgctgct   420

<210> SEQ ID NO 13
<211> LENGTH: 120
<212> TYPE: PRT
<213> ORGANISM: Lama glama

<400> SEQUENCE: 13

Glu Val Gln Leu Val Glu Ser Gly Gly Gly Ser Val Gln Ser Gly Gly
1               5                   10                  15

Ser Leu Arg Leu Ser Cys Ala Ala Ser Gly Tyr Pro Phe Ser Asp Asn
            20                  25                  30

Ala Met Gly Trp Tyr Arg Gln Ala Pro Gly Asn Gln Arg Glu Leu Val
        35                  40                  45

Ala Thr Ile Thr Asn Ser Asn Ser Thr Lys Tyr Ala Asp Ser Val Lys
    50                  55                  60

Gly Arg Phe Thr Ile Ser Arg Asp Ser Ala Lys Asn Thr Ile Tyr Leu
65                  70                  75                  80

Glu Met Asn Ser Leu Lys Pro Glu Asp Thr Ala Ile Tyr Tyr Cys Arg
                85                  90                  95

Ile Glu Arg Thr Gly Arg Thr Ser Ile Lys Trp Thr Tyr Trp Gly Gln
            100                 105                 110

Gly Thr Gln Val Thr Val Ser Ser
        115                 120

<210> SEQ ID NO 14
<211> LENGTH: 360
<212> TYPE: DNA
<213> ORGANISM: Lama glama

<400> SEQUENCE: 14
gaagttcaat tagttgaatc tggtggtggt tctgttcaat ctggtggttc tttacgttta    60
tcttgtgctg cttctggtta tcctttttct gataatgcta tgggttggta tcgtcaagct   120
cctggtaatc aacgtgaatt agttgctact attactaatt ctaattctac taaatatgct   180
gattctgtta aggtcgtttt tactatttct cgtgattctg ctaaaaatac tatttattta   240
gaaatgaatt cttaaaaacc tgaagatact gctatttatt attgtcgtat tgaacgtact   300

```
ggtcgtactt ctattaaatg gacttattgg ggtcaaggta ctcaagttac tgtttcttct    360
```

<210> SEQ ID NO 15
<211> LENGTH: 143
<212> TYPE: PRT
<213> ORGANISM: Lama glama

<400> SEQUENCE: 15

Glu Val Gln Leu Val Glu Ser Gly Gly Gly Ser Val Gln Ser Gly Gly
1               5                   10                  15

Ser Leu Arg Leu Ser Cys Ala Ala Ser Gly Tyr Pro Phe Ser Asp Asn
            20                  25                  30

Ala Met Gly Trp Tyr Arg Gln Ala Pro Gly Asn Gln Arg Glu Leu Val
        35                  40                  45

Ala Thr Ile Thr Asn Ser Asn Ser Thr Lys Tyr Ala Asp Ser Val Lys
    50                  55                  60

Gly Arg Phe Thr Ile Ser Arg Asp Ser Ala Lys Asn Thr Ile Tyr Leu
65                  70                  75                  80

Glu Met Asn Ser Leu Lys Pro Glu Asp Thr Ala Ile Tyr Tyr Cys Arg
                85                  90                  95

Ile Glu Arg Thr Gly Arg Thr Ser Ile Lys Trp Thr Tyr Trp Gly Gln
            100                 105                 110

Gly Thr Gln Val Thr Val Ser Ser Ala Ala Ala Asp Tyr Lys Asp Asp
        115                 120                 125

Asp Asp Lys Gly Ala Ala His His His His His His Gly Ala Ala
    130                 135                 140

<210> SEQ ID NO 16
<211> LENGTH: 429
<212> TYPE: DNA
<213> ORGANISM: Lama glama

<400> SEQUENCE: 16

```
gaagttcaat tagttgaatc tggtggtggt tctgttcaat ctggtggttc tttacgttta     60
tcttgtgctg cttctggtta tccttttct gataatgcta tgggttggta tcgtcaagct    120
cctggtaatc aacgtgaatt agttgctact attactaatt ctaattctac taaatatgct    180
gattctgtta aaggtcgttt tactatttct cgtgattctg ctaaaaatac tatttattta    240
gaaatgaatt cttaaaaacc tgaagatact gctatttatt attgtcgtat tgaacgtact    300
ggtcgtactt ctattaaatg gacttattgg ggtcaaggta ctcaagttac tgtttcttct    360
gctgctgctg attataaaga tgatgatgat aaaggtgctg ctcatcatca tcatcatcat    420
ggtgctgct                                                           429
```

<210> SEQ ID NO 17
<211> LENGTH: 4
<212> TYPE: PRT
<213> ORGANISM: Lama glama

<400> SEQUENCE: 17

Ile Asn Thr Met
1

<210> SEQ ID NO 18
<211> LENGTH: 9
<212> TYPE: PRT
<213> ORGANISM: Lama glama

<400> SEQUENCE: 18

```
Ile Ser Ser Gly Gly Gly Thr Asn Tyr
1               5
```

<210> SEQ ID NO 19
<211> LENGTH: 14
<212> TYPE: PRT
<213> ORGANISM: Lama glama

<400> SEQUENCE: 19

```
Asn Leu His Asn Phe Ser Pro Ile Ser Pro Pro Arg Ser Tyr
1               5                   10
```

<210> SEQ ID NO 20
<211> LENGTH: 4
<212> TYPE: PRT
<213> ORGANISM: Lama glama

<400> SEQUENCE: 20

```
Ile Asn Gly Val
1
```

<210> SEQ ID NO 21
<211> LENGTH: 9
<212> TYPE: PRT
<213> ORGANISM: Lama glama

<400> SEQUENCE: 21

```
Ile Ser Arg Ser Gly Trp Thr Asn Tyr
1               5
```

<210> SEQ ID NO 22
<211> LENGTH: 12
<212> TYPE: PRT
<213> ORGANISM: Lama glama

<400> SEQUENCE: 22

```
Asn Leu His Ser Gly Leu Gly Asn Val Lys Asn Tyr
1               5                   10
```

<210> SEQ ID NO 23
<211> LENGTH: 4
<212> TYPE: PRT
<213> ORGANISM: Lama glama

<400> SEQUENCE: 23

```
Pro Asn Val Met
1
```

<210> SEQ ID NO 24
<211> LENGTH: 9
<212> TYPE: PRT
<213> ORGANISM: Lama glama

<400> SEQUENCE: 24

```
Lys Thr Ser Gly Arg Leu Ser Asn Tyr
1               5
```

<210> SEQ ID NO 25
<211> LENGTH: 9
<212> TYPE: PRT
<213> ORGANISM: Lama glama

<400> SEQUENCE: 25

```
Trp Asp Ser Ala Arg Ser Thr Glu Tyr
```

-continued

```
<210> SEQ ID NO 26
<211> LENGTH: 4
<212> TYPE: PRT
<213> ORGANISM: Lama glama

<400> SEQUENCE: 26

Asp Asn Ala Met
1

<210> SEQ ID NO 27
<211> LENGTH: 9
<212> TYPE: PRT
<213> ORGANISM: Lama glama

<400> SEQUENCE: 27

Ile Thr Asn Ser Asn Ser Thr Lys Tyr
1               5

<210> SEQ ID NO 28
<211> LENGTH: 13
<212> TYPE: PRT
<213> ORGANISM: Lama glama

<400> SEQUENCE: 28

Ile Glu Arg Thr Gly Arg Thr Ser Ile Lys Trp Thr Tyr
1               5                   10

<210> SEQ ID NO 29
<211> LENGTH: 540
<212> TYPE: PRT
<213> ORGANISM: Norovirus

<400> SEQUENCE: 29

Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190
```

```
Asp Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Asp Gly Val Leu
            260                 265                 270

Leu Gly Thr Thr Gln Leu Ser Pro Val Asn Ile Cys Thr Phe Arg Gly
        275                 280                 285

Asp Val Ala His Ile Ala Gly Ser Arg Asn Tyr Thr Met Asn Leu Ala
    290                 295                 300

Pro Leu Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Gly Asp Gly Ser Thr Arg Gly His Lys Ala Thr Val Tyr
            340                 345                 350

Thr Gly Ser Ala Asp Phe Thr Pro Lys Leu Gly Ser Val Gln Phe Gly
        355                 360                 365

Thr Asp Thr Glu Asn Asp Phe Glu Thr His Gln Asn Thr Lys Phe Thr
    370                 375                 380

Pro Val Gly Val Ile Gln Asp Gly Ser Thr Thr His Arg Asn Glu Pro
385                 390                 395                 400

Gln Gln Trp Val Leu Pro Ser Tyr Ser Gly Arg Asn Val His Asn Val
                405                 410                 415

His Leu Ala Pro Ala Val Ala Pro Asn Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Val Gly Asn Gly Thr Gly Arg Arg Arg Val Leu
    530                 535                 540

<210> SEQ ID NO 30
<211> LENGTH: 1629
<212> TYPE: DNA
<213> ORGANISM: Norantea guianensis

<400> SEQUENCE: 30
atgaagatgg caagcaatga tgcaaaccca tctgatggca gcgcagcaaa cctcgttcca      60
gaggttaaca atgaggttat ggctttggag cccgttgttg gcgcagctat tgcagcacct     120
gtagcaggcc aacaaaatgt aattgatccc tggattagaa ataatttcgt tcaagcacct     180
```

-continued

```
ggcggagagt tcacagtaag ccctagaaac gctccaggcg aaatcctatg gagcgcaccc    240
ctcggccctg atctcaatcc ctacctatct catttggcaa gaatgtataa tggctatgca    300
ggcggcttcg aagttcaggt tatcctcgca ggcaacgcat tcaccgcagg aaagattatc    360
ttcgcagcag ttccaccaaa cttcccaact gaaggcttga gtcccagcca ggttactatg    420
ttcccccaca tcatcgtaga tgttaggcaa ctcgaacctg ttttgatccc tttgcctgat    480
gttaggaata acttctatca ctacaatcag agcaatgatt ctaccattaa gttgatcgca    540
atgctctata caccacttag ggcaaataat gctggcgatg atgttttcac agtttcttgt    600
cgtgttctca caagaccaag ccctgatttc gatttcatct tcttggttcc acctacagtt    660
gagagcagaa ccaagccatt cactgttcca atcctcactg ttgaagaaat gaccaatagc    720
agattcccca ttcctttgga aaagctcttc accggcccca gcagtgcatt cgttgttcaa    780
ccacaaaatg gcagatgcac tactgatggc gttctcctcg gcaccaccca actctctcct    840
gttaacatct gcaccttcag aggagatgtt gcacacattg caggcagccg taattacaca    900
atgaatttgg cacctctaaa ttggaacaat tatgatccca cagaagaaat tccagcaccc    960
ctcggaactc cagatttcgt tggaaagatc caaggcatgc tcactcaaac cacaaaggga   1020
gatggctcta cccgtggcca taaggctaca gtttacactg gcagtgcaga tttcactcca   1080
aagctcggca gcgttcaatt cggcactgat acagaaaatg atttcgaaac tcaccaaaac   1140
acaaagttca ccccagttgg cgttatccag gatggcagca ccacccatcg taatgaaccc   1200
caacaatggg ttctccccag ctattctggc agaaatgttc ataatgtaca cctagcacct   1260
gctgtagctc ccaatttccc cggcgaacaa cttcttttct tcaggagcac tatgcccgga   1320
tgcagcggct atcccaacat ggatttggat tgcctcctcc cccaggagtg ggttcagcac   1380
ttctaccaag aggcagctcc agcacaatct gatgttgctc tattgagatt cgttaatcca   1440
gataccggca gggttctctt cgagtgcaag cttcacaaga gcggctatgt tacagttgct   1500
cacaccggcc aacatgattt ggttatcccc cccaatggct atttcaggtt cgatagctgg   1560
gttaaccaat tctacacact tgcacccgtt ggaaatggaa ccggccgtag acgtgttctc   1620
tgagagctc                                                           1629
```

NOROVIRUS ANTIBODY

TECHNICAL FIELD

The present invention relates to a norovirus antibody. More specifically, the present invention relates to the variable domain of the heavy chain of a heavy-chain antibody against a norovirus.

BACKGROUND ART

Norovirus is a pathogenic virus that invades into cells existing from the duodenum to the upper small intestine and causes nonbacterial acute gastroenteritis. Norovirus belongs to Caliciviridae lacking envelopes.

The genome of norovirus is a single-stranded plus-sense RNA of approximately 7.7 kb. A viral protein called VPg covalently binds to the 5'-terminus of the genome, whereas the 3'-terminus thereof is polyadenylated. In the genome of norovirus, the coding regions of three proteins, namely, ORF1, VP1, and VP2 are present, and individual coding regions encode a non-structural protein, a structural protein 1, and a structural protein 2, respectively. As a result of structural analyses, it has been elucidated that 180 VP1 molecules form a dimer, so as to construct a viral structure. Individual VP1 monomers are divided into two domains, namely, a shell domain (S domain) and a protruding domain (P domain), and the P domain is further divided into P1 and P2 subdomains. P2 recognizes blood group antigens functioning as a receptor and a host infectious factor upon infection. As a result of a mutation occurring in the P2 subdomain, a change is generated in the binding of P2 with a blood group antigen (Non Patent Literature 1).

Human noroviruses are classified into three gene groups (GI, GII and GIV) based on the genomic sequences, and reportedly, there are at least 25 types of genotypes. Human norovirus is a norovirus exhibiting high diversity. However, in the past few years, only a small number of strains, such as GII, in particular, GII genotype 4 (GII.4), have caused the epidemicity of the infection (Non Patent Literature 1).

In the United States of America, approximately 2,000,000 people are infected with human norovirus infection every year, and among them, approximately 70,000 patients are hospitalized. In Japan, there are no accurate data, but it is assumed that approximately 10,000 to 20,000 hospitalized patients and, more than approximately 7,000,000 or more infected people are generated every year. The symptoms of a majority of patients with human norovirus infection are ameliorated, but in the case of infant and aged patients, the symptoms become severe, and death cases are sometimes seen. Moreover, there are many cases where the outbreak of human norovirus infection takes place in facilities such as kindergartens and nursing homes. Under such circumstances, the number of outpatients and/or hospitalized patients has reached a considerable scale, and thus, it has posed a great burden on the social insurance system.

As of now, an antiviral therapeutic agent, which is effective for human norovirus, has not been present, and the development of a vaccine has been merely promoted (Patent Literature 1). In view of the foregoing, in the medical field regarding infectious disease, it has been strongly desired to develop and practicalize drugs effective for the treatment and prevention of human norovirus.

CITATION LIST

Patent Literature

Patent Literature 1: JP Patent Publication (Kokai) No. 2015-171363 A

Non Patent Literature

Non Patent Literature 1: Glass et al., N Engl J. Med 361: 1776-1785, 2009
Non Patent Literature 2: Hamers-Casterman et al., Nature 363: 446-448, 1993

SUMMARY OF INVENTION

Technical Problem

Under the aforementioned circumstances, it is an object of the present invention to provide an antibody that reacts against a human norovirus (HuNoV). More specifically, it is the object of the present invention to provide an antibody that inhibits infection of cells with HuNoV (i.e., invasion and/or replication of HuNoV).

Solution to Problem

The present inventors have immunized llamas with VP1 of the HuNoV GII.4 strain as an antigen, and as a result, have succeeded in producing a nanoantibody that inhibits invasion of norovirus VLP (virus-like particle) into intestinal epithelial cells. Moreover, this antibody also inhibited infection of intestinal epithelial cells with a norovirus.

In general, a human antibody is composed of a heavy chain and a light chain. However, in the case of camelids such as llamas, alpacas and camels, a single-stranded antibody only consisting of a heavy chain (i.e., a heavy-chain antibody) is present. Such a heavy-chain antibody can recognize a target antigen and can bind to the antigen, as in the case of an ordinary antibody consisting of a heavy chain and a light chain (Non Patent Literature 2). The variable domain of the heavy chain of a heavy-chain antibody (VHH) is a minimum unit having binding affinity for an antigen, and this variable domain fragment is referred to as a "nanoantibody." The nanoantibody has high heat resistance, digestion resistance and normal temperature resistance, and thus, it is possible to more easily prepare a large amount of the nanoantibody according to a genetic engineering method.

Specifically, the present invention includes the following (1) to (15).
(1) A nanoantibody that binds to a norovirus and inhibits infection of intestinal cells with the norovirus.
(2) The nanoantibody according to the above (1), which is characterized in that the norovirus is HuNoV.
(3) A nanoantibody that inhibits infection of intestinal cells with HuNoV GII.3 and/or HuNoV GII.4, which is characterized in that the amino acid sequences of complementarity-determining regions 1 to 3 (CDR1, CDR2 and CD3) are the following (A), (B), (C) or (D):
(A) CDR1 comprising the amino acid sequence as set forth in SEQ ID NO: 17,
CDR2 comprising the amino acid sequence as set forth in SEQ ID NO: 18, and
CDR3 comprising the amino acid sequence as set forth in SEQ ID NO: 19;
(B) CDR1 comprising the amino acid sequence as set forth in SEQ ID NO: 20, CDR2 comprising the amino acid sequence as set forth in SEQ ID NO: 21, and
CDR3 comprising the amino acid sequence as set forth in SEQ ID NO: 22;
(C) CDR1 comprising the amino acid sequence as set forth in SEQ ID NO 23,
CDR2 comprising the amino acid sequence as set forth in SEQ ID NO: 24, and
CDR3 comprising the amino acid sequence as set forth in SEQ ID NO: 25; and
(D) CDR1 comprising the amino acid sequence as set forth in SEQ ID NO: 26,
CDR2 comprising the amino acid sequence as set forth in SEQ ID NO: 27, and
CDR3 comprising the amino acid sequence as set forth in SEQ ID NO: 28.
(4) A nanoantibody comprising a polypeptide described in the following (a), (b), or (c), and inhibiting infection of intestinal cells with HuNoV GII.3 and/or HuNoV GII.4:
(a) a polypeptide consisting of the amino acid sequence as set forth in SEQ ID NO: 1, SEQ ID NO: 5, SEQ ID NO: 9, or SEQ ID NO: 13;
(b) a polypeptide consisting of an amino acid sequence comprising a substitution, deletion, insertion and/or addition of one or several amino acids with respect to the amino acid sequence as set forth in SEQ ID NO: 1, SEQ ID NO: 5, SEQ ID NO: 9, or SEQ ID NO: 13; and
(c) a polypeptide consisting of an amino acid sequence having a sequence identity of 80% or more to the amino acid sequence as set forth in SEQ ID NO: 1, SEQ ID NO: 5, SEQ ID NO: 9, or SEQ ID NO: 13.
(5) A heavy-chain antibody comprising the nanoantibody according to any one of the above (1) to (4).
(6) A nanoantibody multimer, in which a plurality of the nanoantibodies according to any one of the above (1) to (4) are connected with one another.
(7) A nanoantibody multimer, in which one or a plurality of the nanoantibodies according to any one of the above (1) to (4) are connected with one or a plurality of nanoantibodies each having antigen specificity that is different from the aforementioned nanoantibodies.
(8) A nucleic acid encoding the nanoantibody according to any one of the above (1) to (4).
(9) A nucleic acid as set forth in SEQ ID NO: 2, SEQ ID NO: 6, SEQ ID NO: 10, or SEQ ID NO: 14.
(10) A vector comprising the nucleic acid according to the above (8) or (9).
(11) A cell, into which the vector according to the above (10) is introduced.
(12) A transgenic rice plant, into which the nucleic acid according to the above (8) or (9) is introduced and the nanoantibody is expressed in rice grains thereof.
(13) A rice grain harvested from the transgenic rice plant according to the above (12).
(14) A pharmaceutical composition comprising the nanoantibody, heavy-chain antibody or nanoantibody multimer according to any one of the above (1) to (7).
(15) The pharmaceutical composition according to the above (14), which is characterized in that the disease as a therapeutic or preventive target is norovirus infection.

Advantageous Effects of Invention

According to the present invention, a nanoantibody that inhibits infection of intestinal epithelial cells with HuNoV is provided for the first time.

A medicament or a pharmaceutical composition comprising the nanoantibody or the heavy-chain antibody according to the present invention exhibits the effect of treating and/or preventing infection of HuNoV and various symptoms associated with the infection.

BRIEF DESCRIPTION OF DRAWINGS

FIG. 9 shows KVP-7G5 or KVP-7B4 that does not bind to GII.6-derived VP1 (A); and the results obtained by adding KVP-7G5 or KVP-7B4 and GII.6 (7K) VLP to the intestinal epithelial cell layer (B). FIG. 9B is a view obtained by overlapping a DAPI-stained image, an image stained with an anti-Zo-1 antibody, and a 7K VPL fluorescence image. The scale bar of KVP-7G5 indicates 50 μm, whereas the scale bar of KVP-7B4 indicates 30 μm. The arrow indicates a cell to which VLP has bound.

DESCRIPTION OF EMBODIMENTS

Figure 1:
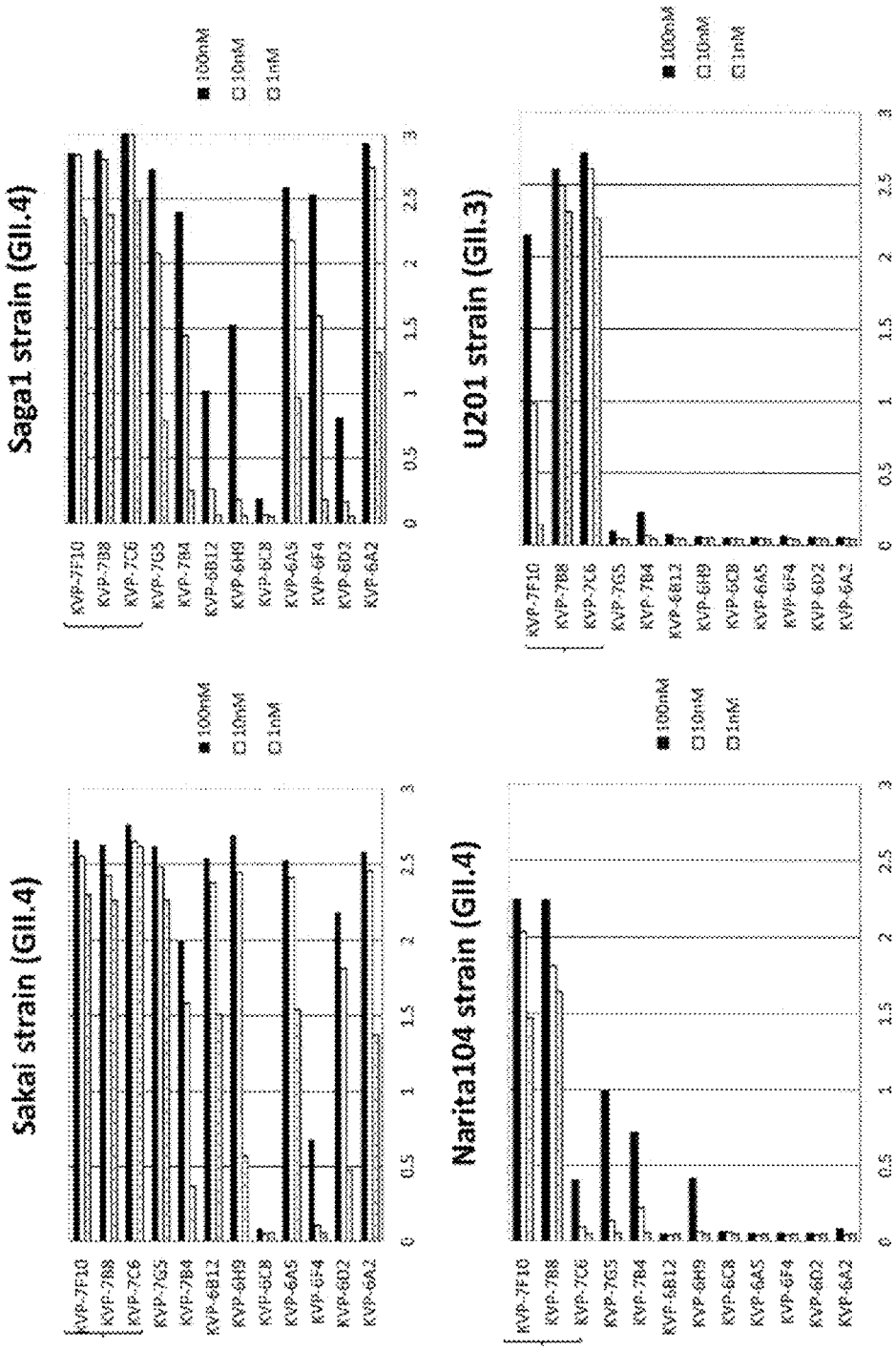
FIG. 1 shows the results of screening for VHH specifically binding to various types of HuNoV GII VP1 (1st screening). The results of ELISA (absorbance at 450 nm) regarding the binding of VP1 derived from GII.4 (Sakai strain, Saga 1 strain, Narita 104 strain) and GII.3 (U201 strain) with various types of VHH are shown.

A first embodiment of the present invention relates to a nanoantibody that binds to a norovirus and inhibits infection of intestinal epithelial cells (for example, small intestinal epithelial cells) with the norovirus (hereinafter also referred to as "the nanoantibody of the present invention"), or a heavy-chain antibody comprising the nanoantibody.

In the embodiment of the present invention, the nanovirus is preferably HuNoV, and examples of the nanovirus may include, but are not limited to, viruses classified into the groups GI, GII and GIV, and preferably, viruses classified into the groups GII.3 and GII.4.

VLP (virus-like particle) mentioned in the present description has a capsid shell consisting of a VP1 protein (i.e., a nanoantibody binding to the VP1 protein also binds to VLP) and also has the same outer shell structure as viruses. However, VLP does not have a gene therein. The VP1 protein means a structural protein 1 that forms the structure of a norovirus. For more information, please refer to, for example, Glass et al., N Engl J Med 361: 1776-1785, 2009.

In the embodiment of the present invention, the nanoantibody of the present invention means a polypeptide that consists of the variable domain of the heavy chain of a heavy-chain antibody (VHH) and can inhibit infection of intestinal epithelial cells with a norovirus.

The nanoantibody of the present invention is, for example, a polypeptide described in the following (a), (b), or (c):

(a) a polypeptide consisting of the amino acid sequence as set forth in SEQ ID NO: 1, SEQ ID NO: 5, SEQ ID NO: 9, or SEQ ID NO: 13;

(b) a polypeptide consisting of an amino acid sequence comprising a substitution, deletion, insertion and/or addition of one or several amino acids with respect to the amino acid sequence as set forth in SEQ ID NO: 1, SEQ ID NO: 5, SEQ ID NO: 9, or SEQ ID NO: 13, and having the activity of binding to HuNoV and inhibiting infection of intestinal cells with the HuNoV; and (c) a polypeptide consisting of an amino acid sequence having a sequence identity of 80% or more to the amino acid sequence as set forth in SEQ ID NO: 1, SEQ ID NO: 5, SEQ ID NO: 9, or SEQ ID NO: 13, and having the activity of binding to HuNoV and inhibiting infection of intestinal cells with the HuNoV.

In the present description, in the case of using the phrase "an amino acid sequence comprising a substitution, deletion, insertion and/or addition of one or several amino acids," the number of substituted, deleted, inserted and/or added amino acids is not particularly limited. For example, approximately 1, 2, 3, 4, 5, 6, 7, 8, 9 or 10 amino acids are preferable. In addition, in the present description, in the case of using the phrase "an amino acid sequence having a sequence identity of 80% or more," the percentage of the sequence identity is not particularly limited, as long as the amino acid sequence has a sequence identity of 80% or more. The sequence identity may be, for example, 90% or more, 91% or more, 92% or more, 93% or more, 94% or more, 95% or more, 96% or more, 97% or more, 98% or more, or 99% or more.

In the above (b) and (c), the site of SEQ ID NO: 1, SEQ ID NO: 5, SEQ ID NO: 9 or SEQ ID NO: 13, on which a substitution, deletion, insertion and/or addition of an amino acid(s) is performed, is desirably a sequence other than the CDR1, CDR2 and CDR3 of each sequence. The above-described substitution, deletion, insertion and/or addition of an amino acid(s) may be a mutation that is originally present in a nucleic acid encoding a protein, or may also be a mutation that is newly introduced by modifying the nucleic acid according to a method known in the present technical field. Such modification, for example, substitution of a specific amino acid residue(s) can be carried out using a commercially available kit (e.g., Mutan™-G (TaKaRa)), etc., by performing substitution of nucleotides according to a known method such as a Gapped Duplex method or a Kunkel method, or a method equivalent thereto.

The polypeptide consisting of the amino acid sequence as set forth in SEQ ID NO: 1, SEQ ID NO: 5, SEQ ID NO: 9 or SEQ ID NO: 13 is the nanoantibody of the present invention. These sequences each have the following CDR1 to CDR3.

(i) SEQ ID NO: 1
CDR1; INTM (SEQ ID NO: 17), CDR2; ISSGGGTNY (SEQ ID NO: 18), CDR3; NLHNFSPISPPRSY (SEQ ID NO: 19)
(ii) SEQ ID NO: 5
CDR1; INGV (SEQ ID NO: 20), CDR2; ISRSGWTNY (SEQ ID NO: 21), CDR3; NLHSGLGNVKNY (SEQ ID NO: 22)
(iii) SEQ ID NO: 9
CDR1; PNVM (SEQ ID NO: 23), CDR2; KTSGRLSNY (SEQ ID NO: 24), CDR3; WDSARSTEY (SEQ ID NO: 25)
(iv) SEQ ID NO: 13
CDR1; DNAM (SEQ ID NO: 26), CDR2; ITNSNSTKY (SEQ ID NO: 27), CDR3; IERTGRTSIKWTY (SEQ ID NO: 28)

The binding ability of the polypeptides described in the above (b) and (c) to VP1 (VLP) can be easily confirmed according to a Western blotting method or an ELISA method. Also, the presence or absence of the activity of inhibiting infection of intestinal epithelial cells (including cells induced from iPS cells and the like) with a norovirus can be easily confirmed by using an intestinal epithelial cell layer prepared as shown in Examples later.

The nanoantibody of the present invention also includes a polypeptide, the amino acid sequences of complementarity-determining regions 1 to 3 (CDR1, CDR2 and CDR3) of which are the following (A), (B), (C), or (D):
(A) CDDR1 comprising the amino acid sequence as set forth in SEQ ID NO: 17,
CDR2 comprising the amino acid sequence as set forth in SEQ ID NO: 18, and
CDR3 comprising the amino acid sequence as set forth in SEQ ID NO: 19;
(B) CDR1 comprising the amino acid sequence as set forth in SEQ ID NO: 20,
CDR2 comprising the amino acid sequence as set forth in SEQ ID NO: 21, and
CDR3 comprising the amino acid sequence as set forth in SEQ ID NO: 22;
(C) CDR1 comprising the amino acid sequence as set forth in SEQ ID NO: 23,
CDR2 comprising the amino acid sequence as set forth in SEQ ID NO: 24, and
CDR3 comprising the amino acid sequence as set forth in SEQ ID NO: 25; and
(D) CDR1 comprising the amino acid sequence as set forth in SEQ ID NO: 26,
CDR2 comprising the amino acid sequence as set forth in SEQ ID NO: 27, and
CDR3 comprising the amino acid sequence as set forth in SEQ ID NO: 28.

Moreover, the embodiment of the present invention includes a heavy-chain antibody comprising the aforementioned "nanoantibody" according to the present invention as a variable domain (i.e., an antibody formed only with a heavy chain), The "heavy-chain antibody" of the present invention may be produced according to a genetic engineering method, or may also be generated by animals generating heavy-chain antibodies, such as camelids.

Furthermore, "the nanoantibody of the present invention" includes not only VHH monomers, but also multimeric "nanoantibodies" ("nanoantibody multimers") prepared by binding a plurality of "the nanoantibodies of the present invention," which are identical to or different from one another, to one another, using a peptide linker or the like.

Further, it may also be possible to produce a nanoantibody multimer, in which one or a plurality of "the nanoantibodies of the present invention" are combined with one or a plurality of other nanoantibodies having different antigen specificity, such as, for example, nanoantibodies reacting against rotavirus (e.g., Tokuhara et al., J Clin Invest. Doi: 10.1172/JCI70266), nanoantibodies binding to norovirus GI, or nanoantibodies reacting against bacterial toxin. The nanoantibody multimer can be produced with reference to, for example, the method described in Schmidt et. al., Clin Vaccine Immuno. 23:774-784 2016.

The nanoantibody of the present invention can be easily produced according to techniques known in the present technical field. Otherwise, the present nanoantibody may also be produced by combining a peptide solid-phase synthesis method with a Native Chemical Ligation (NCL) method.

DNA consisting of a nucleic acid sequence encoding a polypeptide that is the nanoantibody of the present invention (e.g., the sequence as set forth in SEQ ID NO: 2, SEQ ID NO: 6, SEQ ID NO: 10, or SEQ ID NO: 14) is inserted into a suitable expression vector, and the polypeptide is expressed according to an ordinary method, and is then isolated and purified, thereby preparing the nanoantibody of the present invention.

Various host cells, such as, for example, bacterial cells (e.g., *Escherichia coli* B strain, *E. coli* K12 strain, *Corynebacterium ammoniagenes, C. glutamicum, Serratia liquefaciens, Streptomyces lividans, Pseudomonas putida*, etc.); molds (e.g., *Penicillium camembertii, Acremonium chrysogenum*, etc.), animal cells, plant cells, baculoviruses/insect cells, or yeast cells (e.g., *Saccharomyces cerevisiae, Pichia pastoris*, etc.), are used, and the nanoantibody of the present invention can be expressed in these cells. As expression vectors for expressing nanoantibodies, vectors suitable for various types of host cells can be used. Examples of the expression vector that can be used herein may include: pBR322, pBR325, pUC118, pET, etc. (*Escherichia coli* hosts): pEGF-C, pEGF-N, etc. (animal cell hosts) pVL1392, pVL1393, etc. (insect cell hosts, baculovirus vectors); and pG-1, Yep13, pPICZ, etc. (yeast cell hosts). These expression vectors each have a replication origin, a selective marker, and a promoter, which are suitable for each vector. These expression vectors may also have an enhancer, a transcription termination sequence (terminator), a ribosome binding site, a polyadenylation signal, etc., as necessary. Further, in order to facilitate purification of the expressed polypeptide, a nucleotide sequence for fusing a FLAG tag, a His tag, an HA tag, a GST tag, etc. with the polypeptide to express it may be inserted into such an expression vector.

Such an expression vector can be produced by a method known to a person skilled in the art, using a commercially available kit, as appropriate.

When the expressed nanoantibody is extracted from cultured cell masses or cultured cells, the cell masses or the cultured cells are collected by a known method after completion of the culture, and the collected cell masses or cells are then suspended in a suitable buffer. Thereafter, the suspension is subjected to ultrasonic wave, lysozyme treatment and/or freezing-thawing, etc., so that the cell masses or cells are disintegrated. Thereafter, the resultant is subjected to centrifugation or filtration to obtain a soluble extract. An appropriate combination of known separation and/or purification methods is applied to the obtained extract, so as to obtain a polypeptide of interest. Examples of the known separation and/or purification methods that can be used herein may include: methods of utilizing solubility, such as salting-out or a solvent precipitation method; methods of mainly utilizing a difference in molecular weights, such as a dialysis method, an ultrafiltration method, a gel filtration method, or SDS-PAGE; methods of utilizing a difference in electric charges, such as ion exchange chromatography; methods of utilizing specific affinity, such as affinity chromatography (for example, methods, in which when a polypeptide is expressed together with a GST tag, a glutathione-bound carrier resin is used, when a polypeptide is expressed together with a His tag, a Ni-NTA resin or a Co-based resin is used, when a polypeptide is expressed together with a HA tag, an anti-HA antibody resin is used, and when a polypeptide is expressed together with a FLAG tag, an anti-FLAG antibody-hound resin or the like is used); methods of utilizing a difference in hydrophobicity, such as reverse phase high performance liquid chromatography; and methods of utilizing a difference in isoelectric points, such as an isoelectric focusing method.

A second embodiment of the present invention relates to a medicament comprising the nanoantibody of the present invention or the heavy-chain antibody of the present invention. The medicament of the present invention may have an embodiment in which the nanoantibody or heavy-chain antibody of the present invention itself, which is used as an active ingredient, is directly administered. In general, however, the medicament of the present invention is desirably administered in the form of a pharmaceutical composition comprising one or two or more formulation additives, as well as the nanoantibody or the heavy-chain antibody used as an active ingredient. Moreover, as an active ingredient of the medicament or pharmaceutical composition of the present invention, one or more can be selected from the nanoantibodies or heavy-chain antibodies of the present invention, and they can be then used in combination. Furthermore, there may also be used a nanoantibody multimer, in which the nanoantibody of the present invention is combined with one or a plurality of other nanoantibodies having different antigen specificity, such as, for example, nanoantibodies reacting against rotavirus (e.g., Tokuhara et al., J Clin Invest. Doi: 10.1172/JCI70266), nanoantibodies binding to norovirus GI, or nanoantibodies reacting against bacterial toxin. Further, known other drugs may be combined and mixed into the pharmaceutical composition.

The medicament or pharmaceutical composition according to the embodiment of the present invention is not particularly limited. Examples of the dosage form thereof may include a tablet, a capsule, a granule, a powder agent, a syrup agent, a suspending agent, a suppository, an ointment, a cream agent, a gelling agent, a patch, an inhalant, and an injection. These formulations are prepared according to ordinary methods. In the case of a liquid formulation, it may be dissolved or suspended in water or other suitable solvents upon use. In addition, a tablet or a granule may be coated according to publicly known methods. In the case of an injection, it is prepared by dissolving the compound of the present invention in water. Such an injection may also be prepared by dissolving the present compound in a normal saline or a glucose solution, as necessary. Otherwise, a buffer or a preservative may be added to the injection.

A formulation for use in oral administration or parenteral administration is provided in the form of any given formulation. Examples of the formulation form may include: agents for oral administration, such as a granule, a fine granule, a powder agent, a hard capsule, a soft capsule, a syrup agent, an emulsion, a suspending agent, or a liquid agent; injections for intravenous administration, intramuscular administration, subcutaneous administration, etc.; and forms such as an infusion, a transdermal absorbent, a transmucosal absorbent, nasal drops, an inhalant, or a suppository. An injection, an infusion, or the like can also be used by being prepared in the dosage form of powders, such as a freeze-dried form, and then dissolving the powders in a suitable aqueous medium such as a normal saline, upon use.

The types of formulation additives, the ratio of the formulation additives to the active ingredient, or the method for producing the medicament or pharmaceutical composition, which is applied to the medicament or pharmaceutical composition according to the embodiment of the present invention, can be selected, as appropriate, by a person skilled in the art, depending on the form. As formulation additives, inorganic or organic substances, or solid or liquid substances can be used. In general, such formulation additives can be mixed into the present medicament or pharmaceutical composition, in an amount of, for example, 0.1% by weight to 99.9% by weight, 1% by weight to 95.0% by weight, or 1% by weight to 90.0% by weight, based on the weight of the active ingredient. Specific examples of the formulation additives may include lactose, glucose, mannitol, dextrin, cyclodextrin, starch, sucrose, magnesium a luminometasilicate, synthetic aluminum silicate, carboxymethyl cellulose sodium, hydroxypropyl starch, carboxymethyl cellulose calcium, ion exchange resin, methyl cellulose, gelatin, gum Arabic, hydroxypropyl cellulose, hydroxypropylmethyl cellulose, polyvinyl pyrrolidone, polyvinyl alcohol, light anhydrous silicic acid, magnesium stearate, talc, tragacanth, bentonite, beegum, titanium oxide, sorbitan fatty acid ester, sodium lauryl sulfate, glycerin, fatty acid glycerin ester, purified lanolin, glycerogelatin, polysorbate, macrogol, vegetable oil, wax, liquid paraffin, white petrolatum, fluorocarbon, nonionic surfactant, propylene glycol, and water.

In order to produce a solid formulation for oral administration, the active ingredient is mixed with excipient components such as, for example, lactose, starch, crystalline cellulose, calcium lactate, or anhydrous silicic acid to prepare a powder agent. Otherwise, as necessary, binders such as white sugar, hydroxypropyl cellulose or polyvinyl pyrrolidone, disintegrators such as carboxymethyl cellulose or carboxymethyl cellulose calcium, and the like are further added to the aforementioned mixture, and the thus obtained mixture is then subjected to wet or dry granulation, so as to prepare a granule. In order to produce a tablet, these powder agents and granules may be directly subjected to tablet making, or these powder agents and granules, together with a lubricant such as magnesium stearate or talc, may be subjected to tablet making. These granules or tablets can be processed into enteric-coated formulations by being coated with enteric-coating base agents such as hydroxypropylmethyl cellulose phthalate or a methacrylic acid-methyl methacrylate polymer, or can also be processed into sustained release formulations by being coated with ethyl cellulose, carnauba wax, hydrogenated oil, or the like. In addition, in order to produce a capsule agent, a powder agent or a granule is filled into a hard capsule, or the active ingredient is directly coated with gelatin, or is first dissolved in glycerin, polyethylene glycol, sesame oil, olive oil or the like, and is then coated with gelatin, so as to prepare a soft capsule.

In order to produce an injection, the active ingredient is dissolved in distilled water for injection, as necessary, together with a pH adjuster such as hydrochloric acid, sodium hydroxide, lactose, lactic acid, sodium, sodium monohydrogen phosphate or sodium dihydrogen phosphate, and a tonicity agent such as sodium chloride or glucose, and thereafter, the obtained solution is subjected to aseptic filtration, and is then filled into an ampule. Otherwise, mannitol, dextrin, cyclodextrin, gelatin or the like is further added to the resulting solution, followed by vacuum freeze drying, so as to prepare an injection that is soluble at the time of use. Alternatively, lecithin, polysorbate 80, polyoxyethylene hydrogenated castor oil, or the like is added to the active ingredient for emulsification in water, so as to prepare an emulsion for injection.

In order to produce a rectal administration agent, the active ingredient, together with a suppository base agent such as cacao butter, fatty acid tri-, di- and mono-glyceride, or polyethylene glycol, is humidified and is dissolved, and the resultant is then poured into a mold, followed by cooling. Otherwise, the active ingredient may be dissolved in polyethylene glycol, soybean oil, or the like, and may be then coated with a gelatin film.

The applied dose and the number of doses of the medicament or pharmaceutical composition according to the embodiment of the present invention are not particularly limited. The applied dose and the number of doses can be appropriately selected according to the judgment of a doctor or a pharmacist, depending on conditions such as the purpose of preventing and/or treating deterioration and/or progression of a treatment target disease, the type of the disease, and the body weight and age of a patient.

Generally, the dose applied for an adult per day by oral administration is approximately 0.01 to 1,000 mg (the weight of the active ingredient), and this dose can be administered once or divided over several administrations per day, or every several days. In the case of using the medicament or the pharmaceutical composition as an injection, the injection is desirably administered to an adult continuously or intermittently at a daily dose of 0.001 to 100 mg (the weight of the active ingredient).

The medicament or pharmaceutical composition according to the embodiment of the present invention can be prepared as a sustained release formulation, such as an implant tablet and a delivery system encapsulated into a microcapsule, by using a carrier capable of preventing the prompt removal of the agent from the body. As such carriers, biodegradable and biocompatible polymers, such as ethylene vinyl acetate, polyanhydride, polyglycolic acid, collagen, polyorthoester and polylactic acid, can be used. These materials can be easily prepared by a person skilled in the art. Moreover, a liposome suspension can also be used as a pharmaceutically acceptable carrier. Liposome is prepared as a lipid composition comprising, but are not limited thereto, phosphatidylcholine, cholesterol and PEG-derived phosphatidylethanol (PEG-PE), by being passed through a filter with a suitable pore size, so that it can have a size suitable for the use thereof, and it is then purified by a reverse phase evaporation method.

The medicament or pharmaceutical composition according to the embodiment of the present invention may be provided in the form of a kit, together with an instruction manual regarding an administration method and the like. The medicament or the pharmaceutical composition included in the kit is supplied with a vessel, in which the activity of the active ingredient is effectively sustained for a long period of time, the agent and the like are not absorbed on the inside thereof, and the vessel is produced from materials that do not degrade the components. For example, a sealed glass ampule may comprise a buffer or the like that has been enclosed in the presence of neutral and unreactive gas such as nitrogen gas.

Moreover, an instruction manual may be included with the kit. The instruction manual of the present kit may be printed on a paper or the like, or may also be stored in an electromagnetically readable medium such as CD-ROM or DVD-ROM, and may be then supplied.

A third embodiment of the present invention relates to a transgenic rice plant, in which the nanoantibody of the present invention is expressed in rice grains thereof, and the rice grains.

The nanoantibody can be accumulated in rice grains, without losing the properties thereof. The method for producing such a transgenic rice plant, in which the nanoantibody is expressed in rice grains thereof, has already been known. For more information, please refer to, for example, WO2015/011396, Tokuhara et al., J Clin Invest. Doi: 10.1172/JCI70266, and the like (Japanese Patent No. 5616449 regarding the invention made by the present inventors, "Transgenic rice plant capable of expressing nanoantibody," has been held in Japan).

Furthermore, the embodiment of the present invention encompasses a method for treating or preventing norovirus infection or other infections and various symptoms associated with norovirus infection or other infections, wherein the method comprises administering a medicament or a pharmaceutical composition comprising the nanoantibody or heavy-chain antibody of the present invention to a patient and the like.

Herein, the term "treatment" is used to mean prevention or alleviation of the progression and deterioration of the pathologic conditions of a mammal affected with a disease or the like, by which the progression and deterioration of the disease is prevented or alleviated.

On the other hand, the term "prevention" is used to mean that the onset or development of a disease in a mammal that will be likely to be affected with the disease or the like is prevented in advance, and that the onset of various symptoms of the disease is thereby prevented in advance.

The term "mammal" as a therapeutic target means any given animal classified into mammals, and thus, is not particularly limited. Examples of the mammal used herein may include: humans; pet animals such as dogs, cats and rabbits; and livestock animals such as bovines, pigs, sheep and horses. A particularly preferable "mammal" is a human.

The disclosures of all publications cited in the present description are incorporated herein by reference in their entirety. In addition, throughout the present description, when singular terms such as "a," "an," and "the" are used, these terms include not only single items but also multiple items, unless otherwise clearly specified.

Hereinafter, the present invention will be further described in the following examples. However, these examples are only illustrative examples of the embodiments of the present invention, and thus, are not intended to limit the scope of the present invention.

EXAMPLES

1. Preparation of Nanoantibodies Reacting Against Norovirus 1-1. Production of Phage Library Production of the nanoantibody of the present invention was outsourced to QVQ (Utrecht, Netherlands).

Here, preparation of nanoantibodies will be summarized.

Two llamas were immunized with a VP1 antigen solution (SEQ ID NO: 29) 300 µg/injection). The content of VP1 in the antigen solution was 10%, and thus, it means that the llama was immunized with approximately 30 µg of VP1 for a single immunization. Immunization was carried out on the $0^{th}$ (initial immunization day), $14^{th}$, $28^{th}$ and $35^{th}$ days from the initial immunization day. On the $40^{th}$ day from the initial immunization, the immunization was completed, and approximately 200 ml of a blood sample was then collected to prepare peripheral blood lymphocytes (PBL), For the measurement of antibody titer, the serums collected on $0^{th}$ and $44^{th}$ days of the immunization were used. Each well of an immunoplate was coated with 200 ng of VP1 in 50 μl of PBS (4° C. overnight), Thereafter, the plate was washed, and was then blocked with 4% Marvel (in PBS), and the serum was diluted stepwise with 2% Marvel (in PBS) and was then added to each well. Thereafter, each well was washed, and an antibody reacting against VP1 was detected by using a monoclonal antibody reacting against the llamas IgG.

PBLs were prepared from blood collected from the llamas according to Ficoll gradient, and RNA was then prepared from the obtained PBLs according to a phenol-chloroform method. The obtained RNA was reversely transcribed into cDNA, using a reverse transcription enzyme kit (Invitrogen). A DNA fragment encoding IGH (antibody heavy chain) was amplified by using primers binding to leader sequence regions. As a result, a DNA fragment encoding VHH with approximately 700 bp was amplified. This approximately 700 bp DNA fragment was electrophoresed, and was cut out from agarose, followed by extraction. Using the obtained approximately 80 ng DNA fragment as a template, nested PCR was carried out. The amplified fragment was cleaved with BstEII and SfiI, and an approximately 350 bp fragment was then isolated and purified.

The purified approximately 330 ng DNA fragment was inserted into the phagemid pUR8100, and was then introduced into *Escherichia coli* TG1 to produce a VHH phagemid library. Subsequently, from the VHH phagemid library, phages were recovered, so as to prepare a VHH phage library.

From the prepared phage library, human VP1 was used as an antigen (i.e., it was immobilized on the wells of a microplate via an existing antibody, VP1 antibody), and two rounds of biopanning were performed according to an ELISA method, so that phage clones binding to the human VP1 were selected.

1-2. Screenings for VHH Binding to Human Norovirus VP1 (First and Second Screenings)

From the selected phage clones, VHH DNA was amplified according to PCR, and *Escherichia coli* (*E. coli* TG1) were then transformed with pMEK222 (comprising a FLAG tag and a His tag), into which the amplified DNA had been inserted. *Escherichia coli* retaining an insert (VHH DNA fragment) were screened, and the sequence of VHH was determined. A VHH polypeptide expressed in *Escherichia coli* was purified by passing the cell extract through a Co resin.

In order to confirm the specificity and cross activity of the obtained VHH, the VP1 of each of the genotypes belonging to the human norovirus GII (GII.2 (MK04 strain), GII.3 (U201 strain), GII.4 (Sakai strain, Saga 1 strain, and Narita 104 strain), GII.6 (7K strain), and GII.17 (Kawasaki 308 strain)) was used as an antigen, and ELISA was carried out.

Each VP1 (100 ng/well) in a concentration of 1 μg/ml that had been diluted with PBS on the previous day was added to a microplate well, and it was then immobilized at 4° C. overnight. After completion of the immobilization, the resultant was washed with PBST (250 μl/well) five times, and was then blocked with 1% BSA-PBST (200 μl/well) at room temperature for 1.5 hours. Thereafter, the resultant was washed with PBST (250 μl/well) three times, and each nanoantibody that had been diluted to 1 nM, 10 nM and 100 nM with a blocking buffer was added in an amount of 100 μl/well to the plate. The obtained mixture was incubated at room temperature for 2 hours. After completion of the incubation, the resultant was washed with PBST (250 μl/well) five times, and thereafter, HRP conjugated anti-FLAG (M2) (SIGMA) that had been 10,000 times diluted with PBST was added in an amount of 100 μl/well to the plate.

The obtained mixture was incubated at room temperature for 1 hour. After completion of the incubation, the reaction mixture was washed with PBST (250 μl/well) five times, and a substrate solution (TMB Microwell Peroxidase Substrate System, KPL) was then added in an amount of 100 μl/well to the plate, followed by reacting at room temperature for 5 minutes. Thereafter, 2 N sulfuric acid was added in an amount of 50 μl/well to the plate, so that coloration was terminated. Thereafter, the absorbance at 450 nm was measured using a microplate reader (BIO-RAD).

Figure 2:
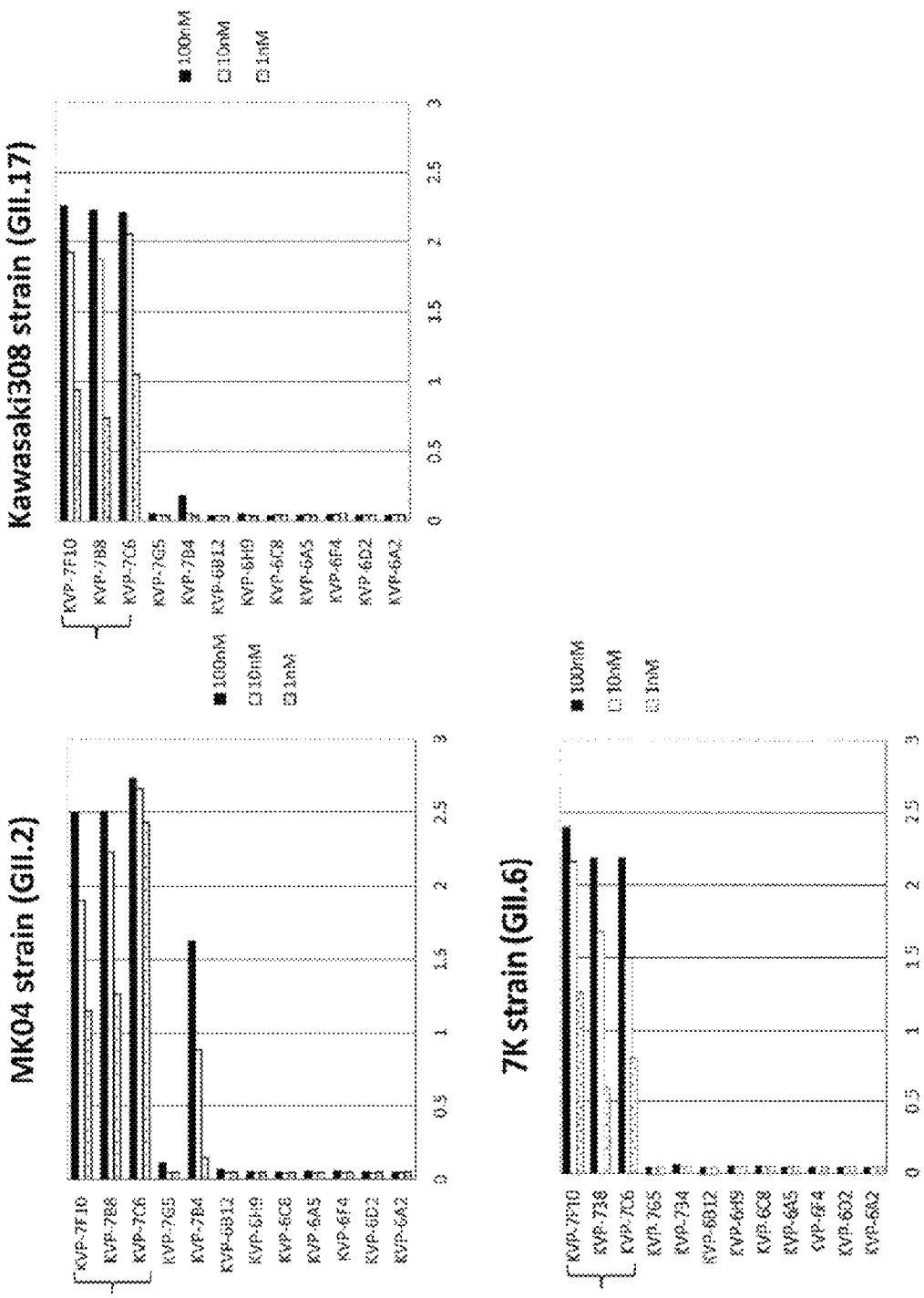
FIG. 2 shows the results of screening for VHH specifically binding to various types of HuNoV GII VP1 (1st screening). The results of ELISA (absorbance at 450 nm) regarding the binding of VP1 derived from GII.2 (MK04 strain), GII.6 (7K strain) and GII.17 (kawasaki 308 strain) with various types of VHH are shown.
Figure 3:
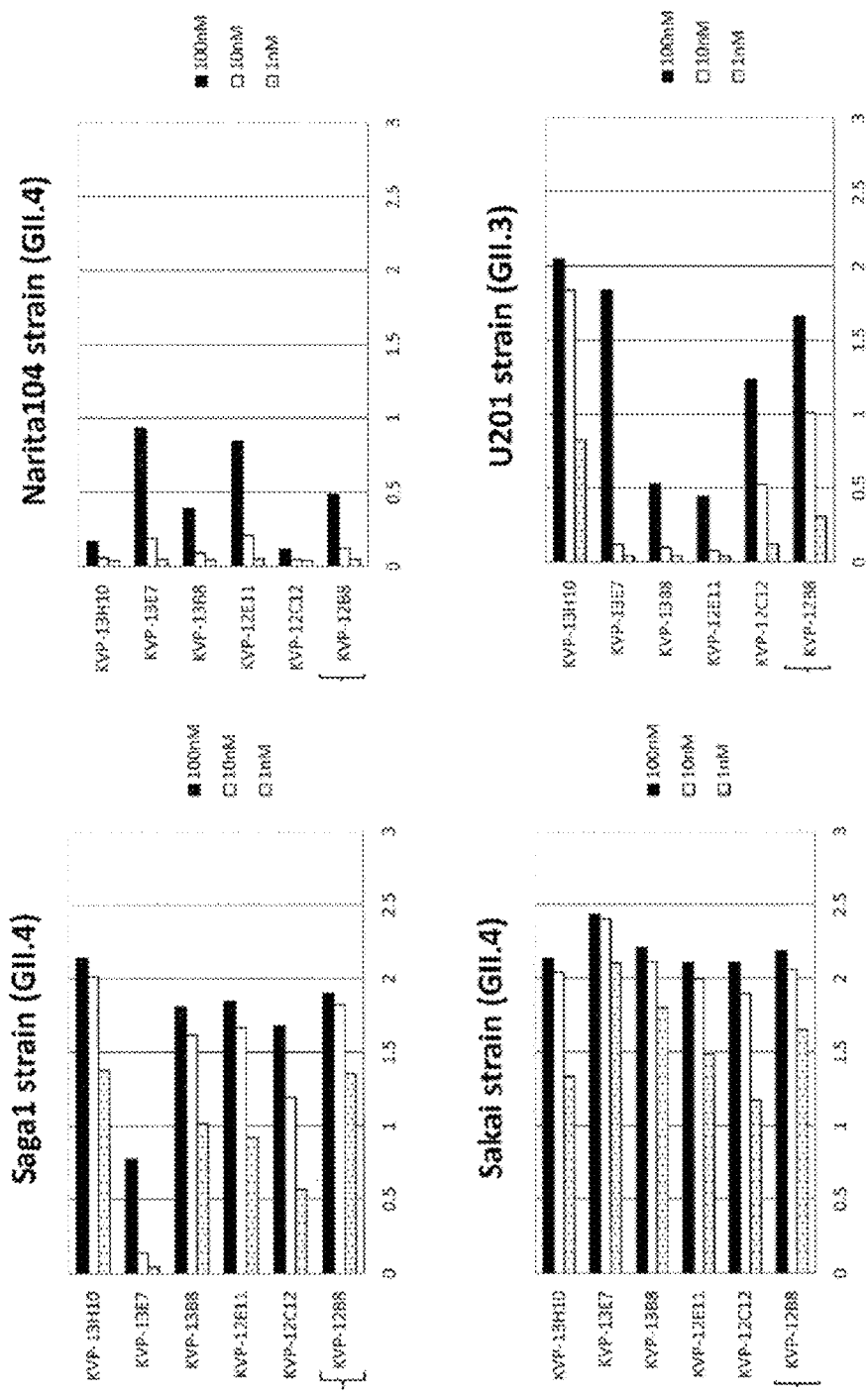
FIG. 3 shows the results of screening for specifically binding to various types of HuNoV GII VP1 (2nd screening). The results of ELISA (absorbance at 450 nm) regarding the binding of VP1 derived from GII.4 (Sakai strain, Saga 1 strain, Narita 104 strain) and GII.3 (U201 strain) with various types of VHH are shown.
Figure 4:
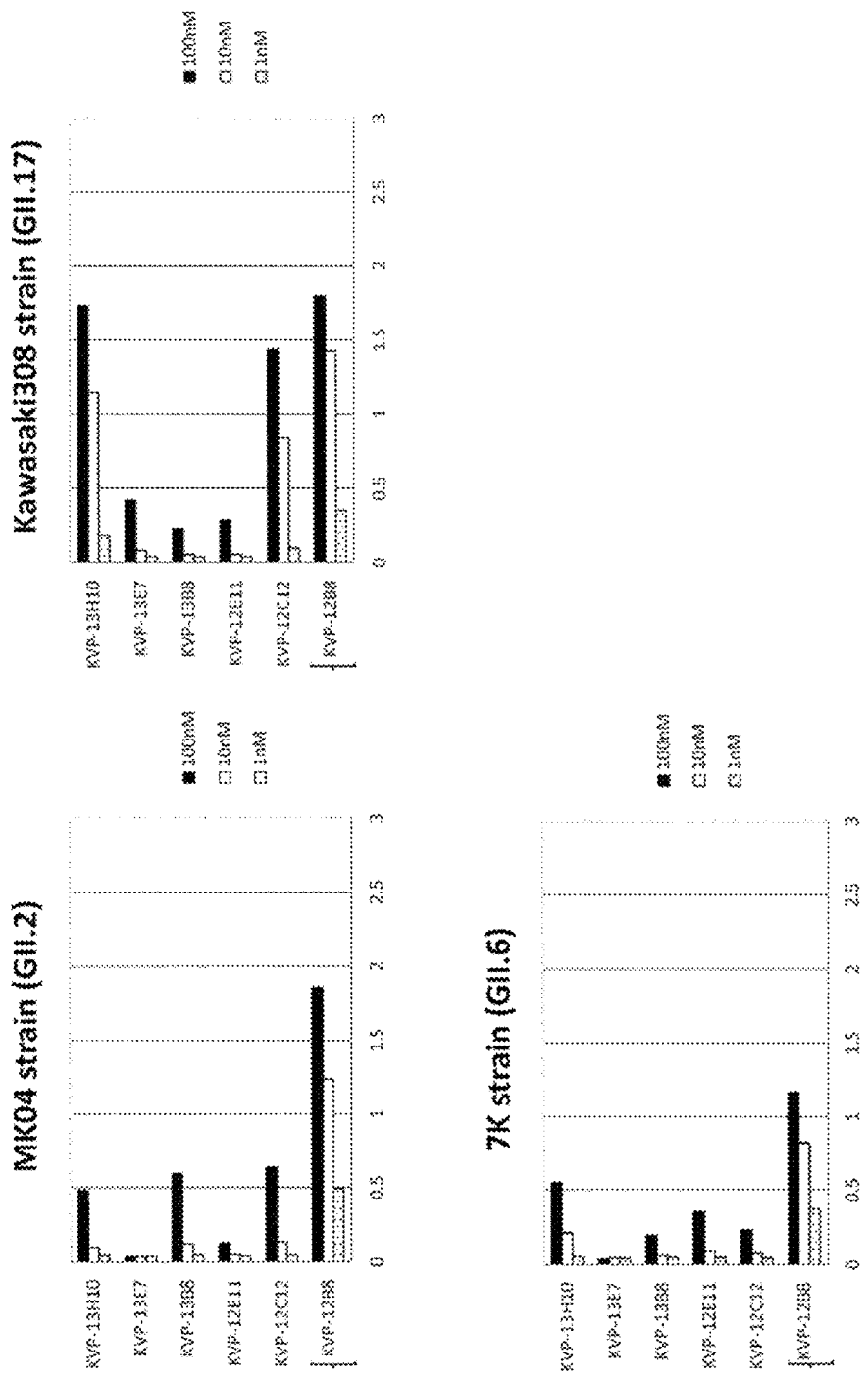
FIG. 4 shows the results of screening for VHH specifically binding to various types of HuNoV GII VP1 (2nd screening). The results of ELISA (absorbance at 450 nm) regarding the binding of VP1 derived from GII.2 (MK04 strain), GII.6 (7K strain) and G11.17 (kawasaki 308 strain) with various types of are shown.

The aforementioned step was carried out twice. As a result of the first screening, KVP-7F10 (SEQ ID NO: 1), KVP-7B8 (SEQ ID NO: 5), and KVP-7C6 (SEQ ID NO: 9), which specifically bound to VP1 derived from GII.4 (Sakai strain, Saga 1 strain and Narita 104 strain), GII.3 (U201 strain), GII.2(MK04 strain), GII.6 (7K strain), and GII.17 (Kawasaki 308 strain), were obtained (FIG. 1 and FIG. 2). Further, as a result of the second screening, KVP-12B8 (SEQ ID NO: 13) specifically binding to VP1 derived from GII.4 (Sakai strain, Saga 1 strain and Narita 104 strain), GII.3 (U201 strain), GII.2 (MK04 strain), GII.6 (7K strain), and GII.17 (Kawasaki 308 strain), was obtained (FIGS. 3 and 4). It is to be noted that the nanoantibodies obtained herein had low binding ability to GI.4 (Chiba strain) and GI.6 (W18 strain).

CDR1 to CDR3 of the nanoantibodies consisting of the amino acid sequences as set forth in SEQ ID NO: 1, SEQ ID NO: 5, SEQ ID NO: 9 and SEQ ID NO: 13 were determined with reference to the CDR sequences of VH-1 of rotavirus (Stability of llama heavy-chain antibody fragments under extreme conditions Chapter 4 "Decreasing trypsin susceptibility of single domain antibodies: implications for structural stability:"/Edward Dolk-[S.1.]: [s.n.], 2004-Universiteit Utrecht ISBN nr: 90-393-3643-1 (dspacelibrary.uu.n1/bitstream/handle/1874/25 1/inhoud.htm; jsessionid=ADE7F83BC64DB071D 664C9CF587B01E5?sequence=16), Spinelli et al., Biochemistry 39: 1217-1222, 2000).

2. Linear Epitope Mapping (Western Blot)

In order to examine the epitopes of the obtained nanoantibodies individual domains of VP1 (SEQ ID NO: 29) of human norovirus (GII.4 strain), namely, a full-length P domain (amino acids at positions 224 to 540 in SEQ ID NO: 29), P1-1 and P2 (amino acids at positions 224 to 411 in SEQ ID NO: 29), P2 (amino acids at positions 271 to 411 in SEQ ID NO: 29), and P1-2 (amino acids at positions 412 to 540 in SEQ ID NO: 29) were allowed to express in *Escherichia coli*.

Specifically, using the VP1 gene (SEQ ID NO: 30), the nucleotide sequence of each domain was amplified by PCR, so that an EcoRI cleaved sequence+GATG was added to the 5'-terminus and an XhoI cleaved sequence was added to the 3'-terminus, thereby producing a pET20b(+) expression vector (wherein 6×His was added to the C-terminus).

*Escherichia coli* retaining the expression vector of each domain was cloned, and *Escherichia coli* Rosetta2 pLysS (Novagen 71403) was then transformed according, to a heat shock method. The thus transformed *Escherichia coli* were subjected to shaking culture in a SOC medium. The obtained culture was seeded on an LB-Amp agar medium, and was then cultured at 37° C. Thereafter, the colony was seeded on a liquid medium and was then cultured. The obtained culture solution was defined as a glycerol stock.

Figure 5:
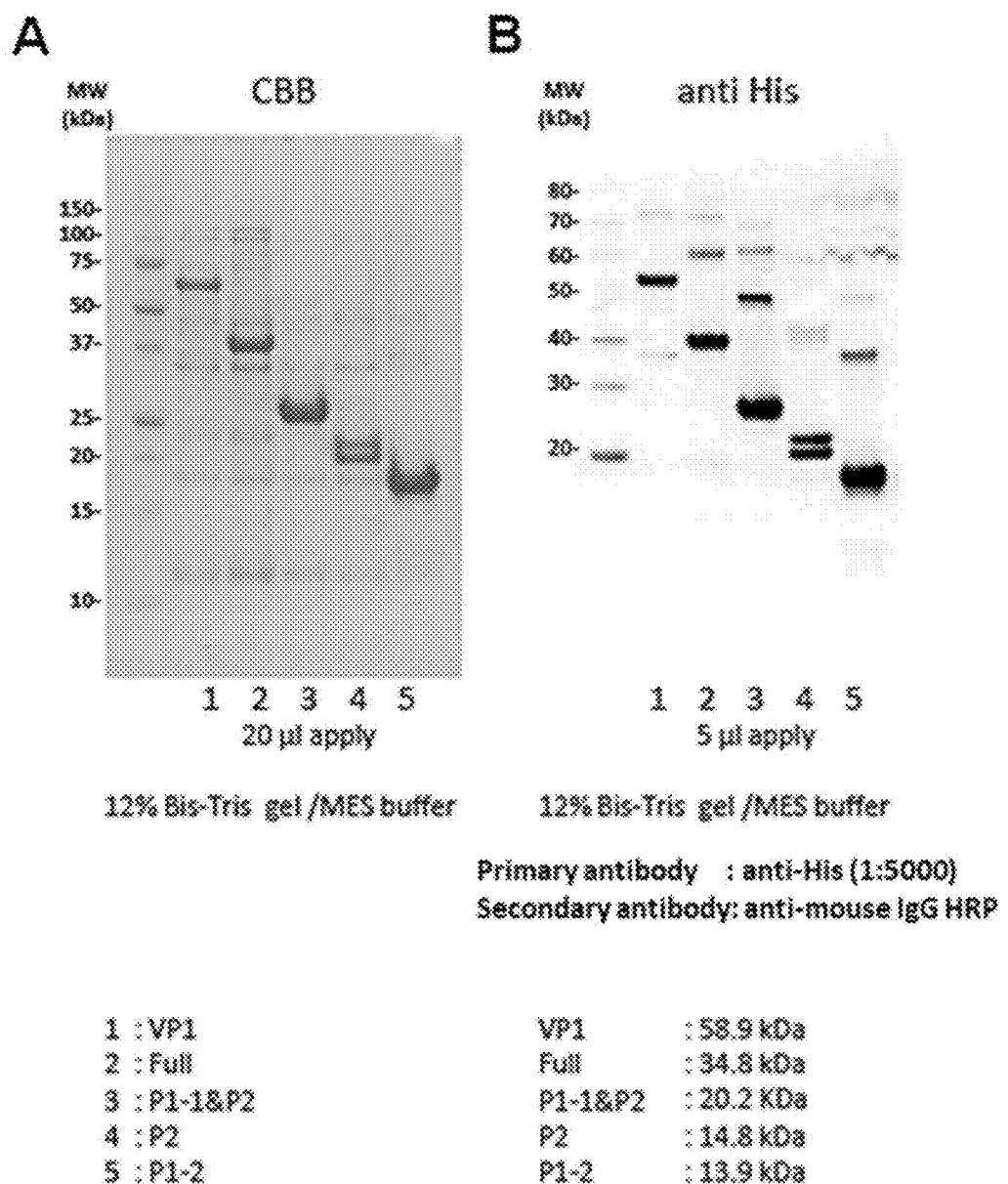
FIG. 5 shows the results of confirmation of the expression of individual domains of HuNoV (GII.4 strain) VP1. The full-length P domain, P1-1 & P2 domains, P2 domain, and P1-2 domain of VP1, which were expressed in *Escherichia coli*, were electrophoresed (A), and they were then subjected to Western blotting with an anti-His tag antibody (B).

Subsequently, the stock was cultured, and the expression of a protein was then confirmed by induction with 1 mM IPTG. The recovered cell mass was dissolved in a lysis buffer containing 6 M urea, and each domain protein was then extracted. The extracted domains were each purified with His-tag (metal chelate affinity chromatography) in a state denatured with 6 M urea. The obtained each protein was confirmed by Western blot using an anti-His antibody (FIG. 5).

Next, using the expressed each domain, the linear epitope mapping of each nanoantibody was carried out.

The purified each domain protein and a molecular weight marker were added in each amount of 5 µl/lane, so that they were separated by SDS-PAGE. Thereafter, gel was transferred on a membrane. After completion of the transcription, the membrane was immersed in 5% skim milk-TBST and Was then blocked at room temperature for 1 hour. The nanoantibodies prepared in 1 above were each diluted with TBST to a concentration of 10 µg/ml, and were then reacted on the membrane after completion of the transfer at room temperature for 1.5 hours. After completion of the reaction, the membrane was washed in TBST at room temperature for 5 minutes three times. After completion of the washing, Monoclonal Anti-FLAG M2-HRP antibody that had been 3,000 times diluted with TBST was added to the membrane, and they were then reacted at room temperature for 1 hour. After completion of the reaction, the reaction mixture was washed in TBST at room temperature for 5 minutes three times. Subsequently, a substrate was added to the membrane, and was then reacted at room temperature for 5 minutes. After that, using Image Quant LAS 4000mini, chemiluminescence was measured.

Figure 6:
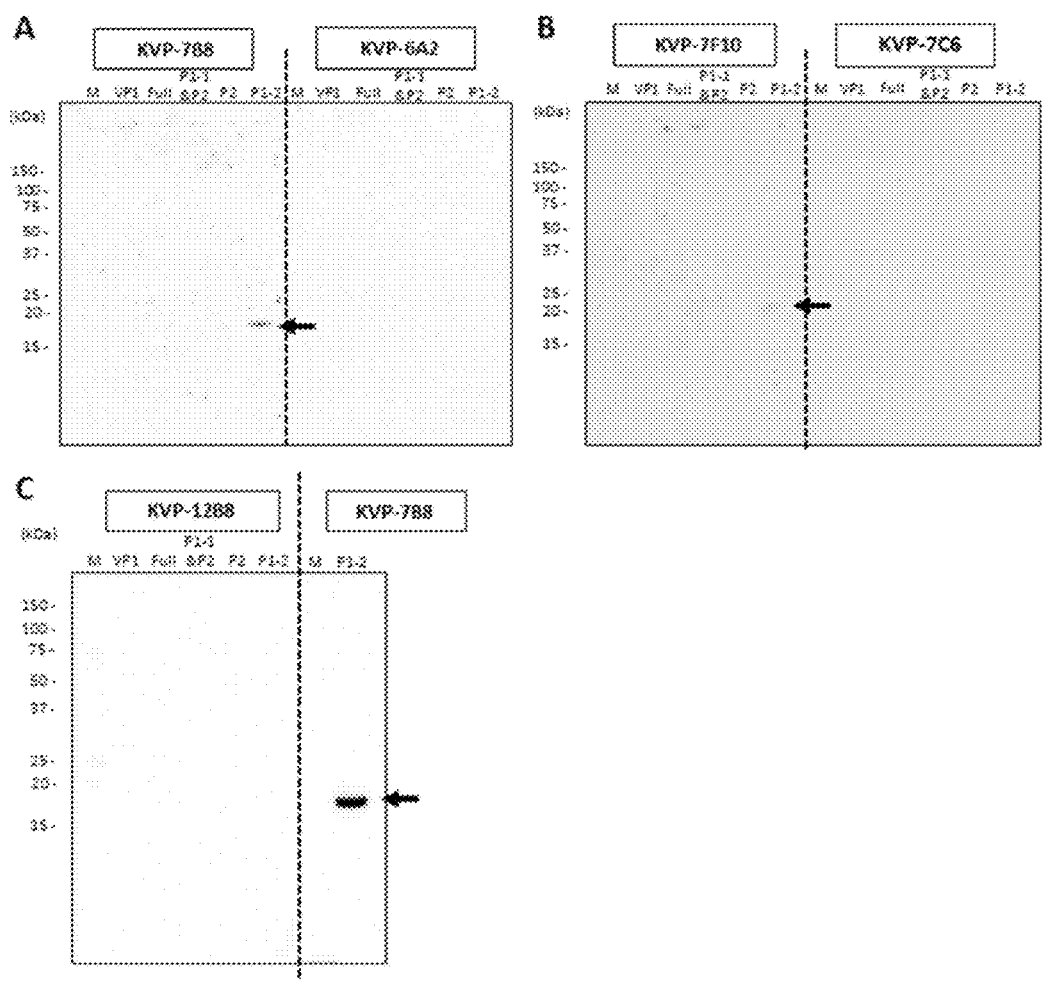
FIG. 6 shows the results of the linear epitope mapping of the nanoantibodies (KVP-7F10, KVP-7C6 and KVP-7B8). Individual domains of VP1 shown in FIG. 5 were subjected to Western blotting with KVP-7B8 (A), KVP-7F10 (B), KVP-7C6 (B), and KVP-12B8 (C). The arrow indicates a band of the VP1 P1-2 domain detected with the nanoantibodies.

The nanoantibodies KVP-7F10 (FIG. 6B) and KVP-7B8 (FIGS. 6A and 6C) obtained by the first screening reacted with P1-2, but KVP-7C6 did not react with P1-2 (FIG. 6B). The nanoantibody IC VP-12B8 obtained by the second screening did not react with P1-2, either (FIG. 6C). Under the same conditions as mentioned above, KPV-7B8 certainly reacted with P1-2 (FIG. 6C). It was considered that, at least, 7F10 and 7B8 would bind to a portion near here. However, even if they did not hind to this linear sequence, it could not be concluded that they did not exhibit binding ability to a region near here. Beside, Hansnian et al. have reported that a mouse monoclonal antibody reacting against GII common binds to a region around P1-2 (J Virol. 2012 April; 86(7): 3635-46. doi: 10.1128/JVI. 06868-11. Epub 2012 Jan. 25.).

3. Studies Regarding Effects of Nanobodies to Inhibit Invasion or Norovirus

3-3. Production of Monolayered Intestinal Epithelial Cell Layer

In order to establish culturable human monolayered epithelial cells, newborn skin-derived human iPS cells (TkDN4-M; furnished from Dr. Masahiro OTSU, TSU Division of Stem Cell Processing, Center for Stem Cell Biology and Regenerative Medicine, ISMUT, Tokyo University/ Stem Cell Bank) were cultured in a medium supplemented with Activin A, Wnt3a and the like for 3 days, so that the iPS cells were allowed to differentiate into endoderm cells, which were further cultured in a medium supplemented with FGF4 and Wnt3a for 3 to 4 days, so that differentiation of the cells into the lower digestive tract was induced. When a spherical cell mass (spheroid) having a tubular structure was formed, it was subjected to a three-dimensional culture in a medium supplemented with R-spondin 1, EGF, etc. for 2 weeks to obtain organoids. Thereafter, the obtained organoids were further sub-cultured in a medium supplemented with Wnt3a, HGF, etc., so that the organoids were allowed to proliferate. The thus proliferating organoids were disintegrated, and stem cells were collected. Thereafter, the stem cells were seeded on Transwell (registered trademark) (24-well) and were then cultured for 10 days, so as to establish monolayered human intestinal epithelial cells.

It is to be noted that induction of organoids and monolayered epithelial cells according to biopsy from living bodies can be carried out with reference to Ettayebi et al., please refer to Science 353: 1387-1393, 2016, etc. On the other hand, induction of organoids from iPS cells can be carried out with reference to McCracken et al., Nat. protocol. 6: 1920 2011, etc.

3-2. Immunohistostaining

3-2-1. Whole Mount Staining

In order to confirm inhibition of the binding of VLP to epithelial cells by nanoantibodies, a mixed solution of GII.6 (7K) VLP (Virus-like particle) and a nanoantibody (molar ratio: 1:1, 1:0.1 and 1:0.01), and only VLP (500 ng) used as a positive control (furnished from Dr. Kazuhiko KATAYAMA of Virus Department, National Institute of Infectious Diseases, (currently, a professor of Kitasato Institute for Life Sciences, Kitasato University)), which had previously been pre-incubated at room temperature for 1 hour, were each added in an amount of 100 µl/well to epithelial cells that had been monolayered on the Transwell. The thus obtained mixture was incubated at 37° C. for 3 hours. After completion of washing, the reaction mixture was fixed with 4% PFA and was then subjected to a dialysis treatment with 0.5% Triton X-100—PBS. Thereafter, the Transwell membrane was cut out from the back. The membrane was immersed in a 5% Goat Serum-NETG buffer (150 mM NaCl, 5 mM EDTA, 50 mM Tris-HCl, 0.05% Triton X-100, and 0.25% gelatin), so that it was blocked at room temperature for 1 hour. After that, the resulting membrane was immersed in a primary antibody (anti-Zo-1 (Invitrogen); Zo-1 is a molecule existing in the tight junction of epithelial cells, and serves as a marker for intercellular adhesion formation) that had been 150 times diluted with an NETG buffer, and was reacted at 4° C. overnight. After completion of the reaction with the primary antibody, the resulting membrane was washed, and was then immersed in a reaction solution prepared by diluting GII.6 (7K) VLP (100 times) labeled with HiLyte Fluor™ 555 by employing HiLyte Fluor™ 555 Labeling Kit-NH2 (DOJINDO LABORATORIES), DyLight™ 488 conjugated anti-Mouse IgG (Jackson, 400 times) used as a secondary antibody, and DAPI (1000 times) with an NETG buffer, so that it was reacted at room temperature for 3 hours. Thereafter, the resulting membrane was washed with PBST and PBS, and was then enclosed. Then, using a confocal laser microscope, fluorescence was detected.

Figure 7:
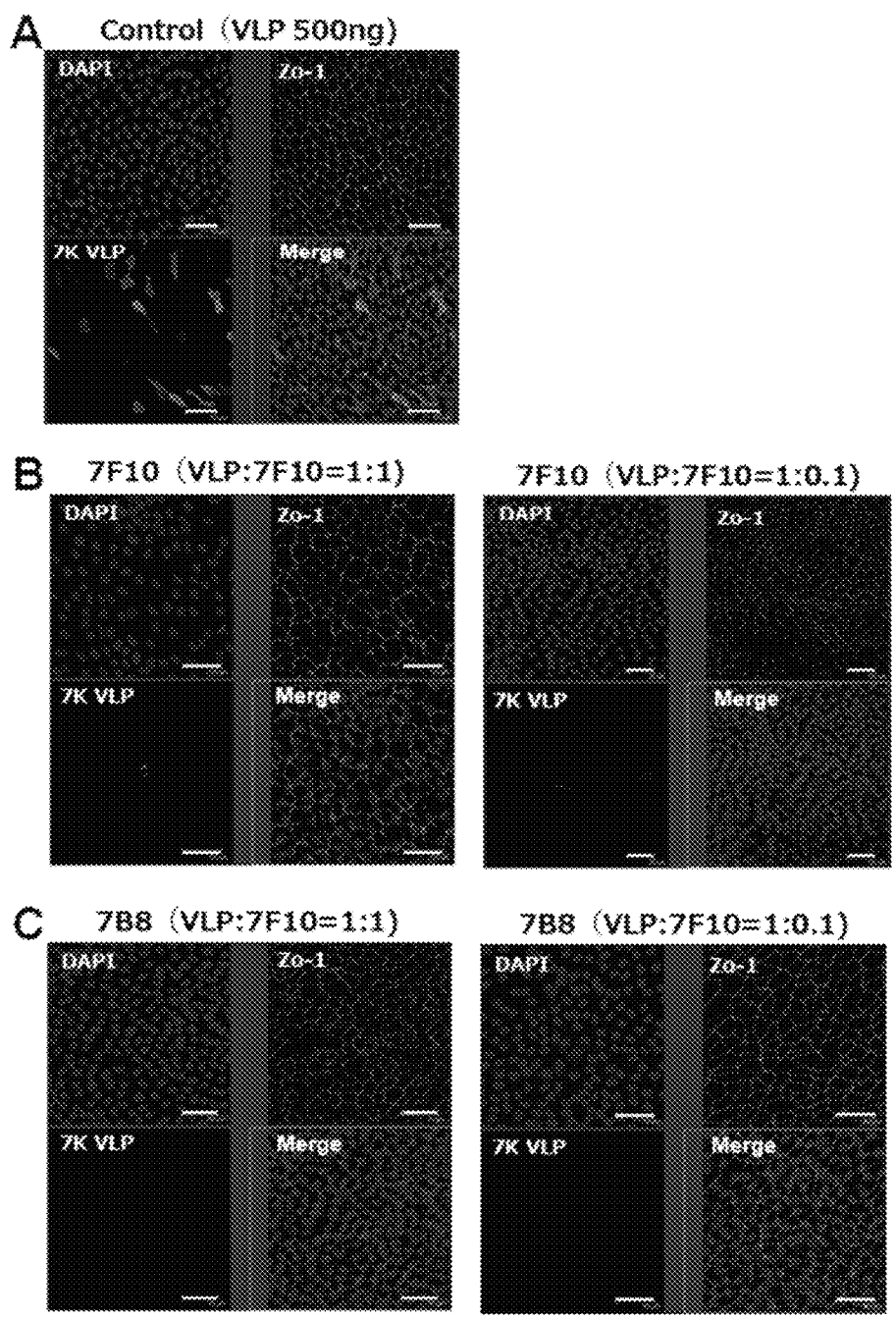
FIG. 7 shows the influence of the nanoantibodies (KVP-7F10 and KVP-7B8) on the binding of HuNoV VLP to intestinal epithelial cells. The results obtained by adding only GII.6 (7K) VLP (A). GII.6 (7K) VLP and KVP-7F10 (B), or GII.6 (7K) VLP and KVP-7B8 (C) to the intestinal epithelial cell layer are shown. The scale bar indicates 50 μm. DAPI: DAPI staining: Zo-1: staining with an anti-Zo-1 antibody 7K VPL: GII.6 (7K) VLP labeled with HiLyte Fluor™ 555 pigment; and Merge: a view obtained by overlapping the fluorescence images of DAPI, Zo-1 and 7K VPL.

FIG. 7 shows the results obtained by examining the inhibitory ability of KVP-7F10 and IVP-7B8 towards the binding of VLP to epithelial cells. As shown in "7K VLP"

and "Merge" of FIG. 7A, in the case of only VLP as a control, the fluorescence of VLP binding to epithelial cells was detected. In contrast, in a case where KVP-7F10 and KVP-7B8 were added to GII.6 (7K) VLP at molar ratios of 1:1 and 1:0.1, the fluorescence of VLP was hardly detected (see "7K VLP" and "Merge" in FIGS. 7B and 7C). Accordingly, it was demonstrated that KVP-7F10 and KVP-7B8 effectively inhibit the binding of GII.6 (7K) VLP to epithelial cells.

Figure 8:
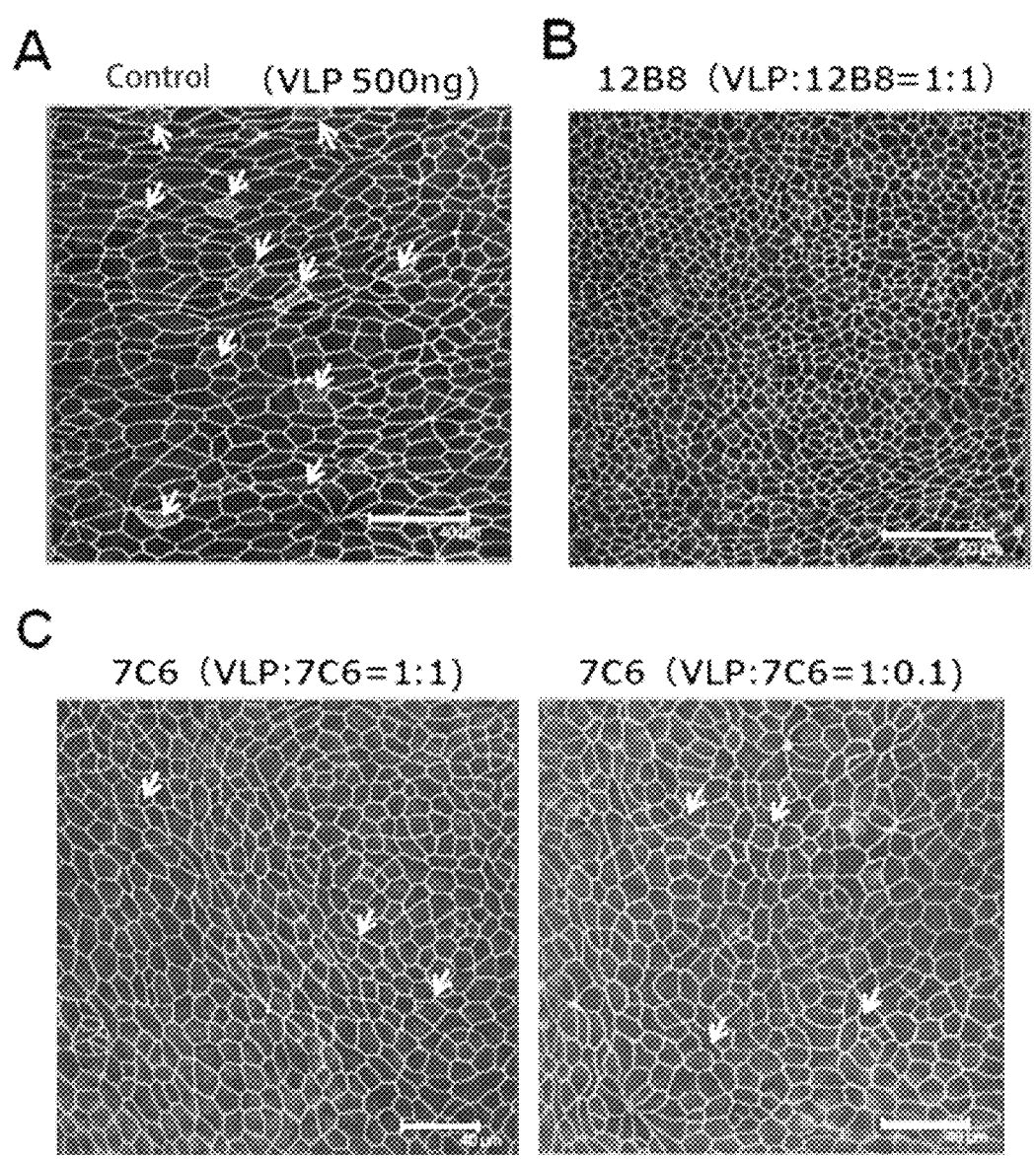
FIG. 8 shows the influence of the nanoantibodies (KVP-12B8 and KVP-7C6) on the binding of HuNoV VLP to intestinal epithelial cells. The results obtained by adding only GII.6 (7K) VLP (A), GII.6 (7K) VLP and KVP-12B8 (B), or GII.6 (7K) VLP and KVP-7C6 (C) to the intestinal epithelial cell layer are shown. Each view shows the overlapping of a DAPI-stained image, an image stained with anti-Zo-1 antibody, and a 7K VPL fluorescence image. The scale bar indicates 40 μm in FIGS. 8A and 8C, and the scale bar indicates 50 μm in FIG. 8B. The arrow indicates a cell to which VLP has bound.

FIG. 8 shows the results obtained by examining the inhibitory ability of KVP-12B8 and KVP-7C6 towards the binding of VLP to epithelial cells. In the case of only VLP as a control, the fluorescence of VLP was detected in the cells indicated with the arrows in FIG. 8A. In contrast, in a case where KVP-12B8 was added to GII.6 (7K) VLP at a molar ratio of 1:1, the fluorescence of VLP was hardly detected (FIG. 8B). In addition, in a case where KVP-7C6 was added to GII.6 (7K) VLP at molar ratios of 1:1 and 1:0.1, the fluorescence of VLP was slightly observed, but it is found that the binding of VLP to the cells was almost inhibited in comparison to the control (FIG. 8C).

Figure 9:
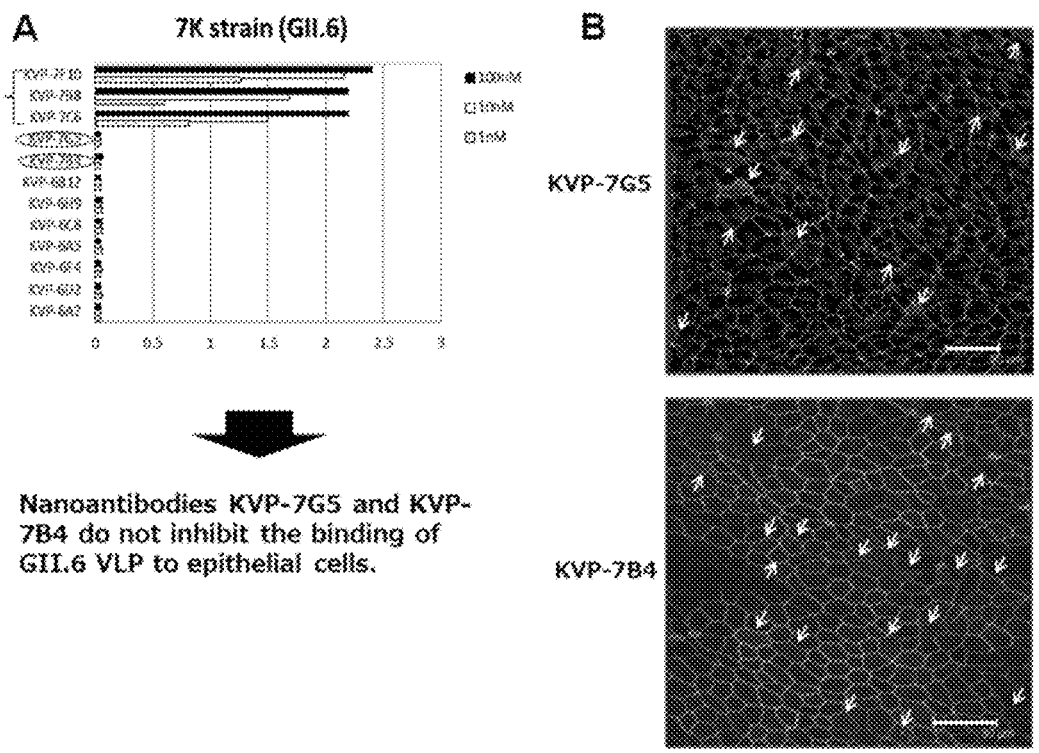
FIG. 9 shows the influence of the nanoantibodies (KVP-7G5 and KVP-7B4) on the binding of HuNoV VLP to intestinal epithelial cells.

From the aforementioned results, it was demonstrated that KVP-7F10, KV P-78, KVP-12B8, and KVP-7C6 effectively inhibit the binding of GII.6 (7K) VLP to epithelial cells. It is to be noted that KVP-7G5 and KVP-7B4 (FIG. 9A) that did not bind to GII.6 (7K) VLP did not inhibit the binding of the VLP to epithelial cells (FIG. 9B).

3-2-2. Confirmation of Invasion of VLP into Epithelial Cells (Frozen Section Staining)

In order to confirm incorporation of VLP into epithelial cells. GII.6 (7K) VLP (300 ng) was added in an amount of 100 μl/well to epithelial cells that had been monolayered on the Transwell, and the obtained mixture was then incubated at 37° C. for 3 hours. After completion of washing, the reaction mixture was fixed with 10% formalin and was then washed with 70% EtOH, and the membrane was cut out from the back. A frozen block embedded in O.C.T. Compound (Sakura Finetek Japan. Co., Ltd.) was produced, and a frozen section with a size of 7 to 8 μm was then produced using a cryostat.

5% Goat Serum-NETG buffer (150 mM NaCl, 5 mM EDTA, 50 mM Tris-HCl, 0.05% Triton X-100, and 0.25% gelatin) was added to the frozen section, and the frozen section was then blocked at room temperature for 1 hour. Thereafter, a primary antibody (anti-Zo-1 (Invitrogen)) that had been 150 times diluted with an NETG buffer was added to the frozen section, and the obtained mixture was then reacted at 4° C. overnight. After completion of the reaction with the primary antibody, the resulting membrane was washed, and was then immersed in a reaction solution prepared by diluting GII.6 (7K) VLP (100 times) labeled with HiLyte Fluor™ 555 by employing HiLyte Fluor™ 555 Labeling Kit-NH2 (DOJINDO LABORATORIES), DyLight™ 488 conjugated anti-Mouse IgG (Jackson, 400 times) used as a secondary antibody, and DAPI (1000 times) with an NETG buffer, so that it was reacted at room temperature for 3 hours. Thereafter, the resulting membrane was washed with PBST and PBS, and was then enclosed. Then, using a confocal laser microscope, fluorescence was detected (FIG. 10).

Figure 10:
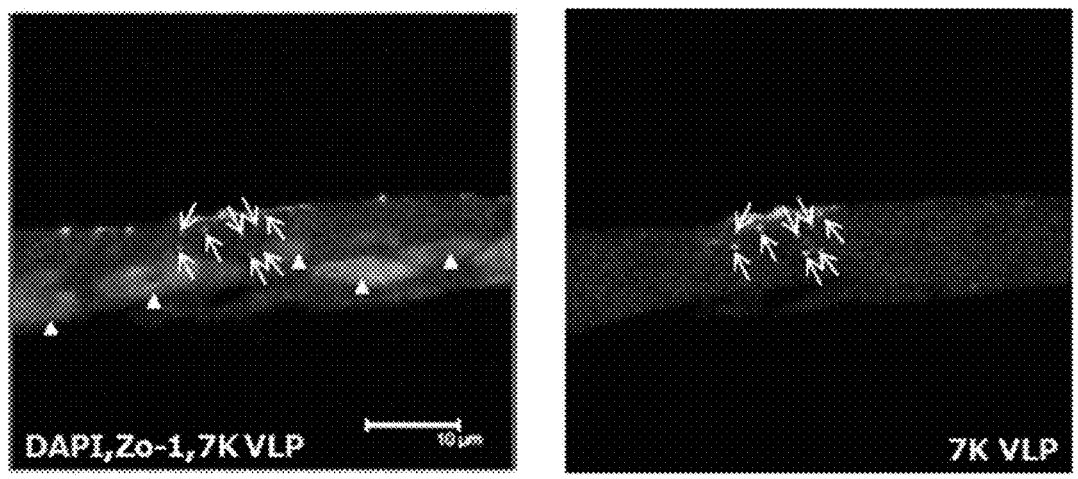
FIG. 10 shows the results of confirmation of the invasion of HuNoV GII.6 (7K) VLP into intestinal epithelial cells. The results obtained by staining frozen sections of monolayered epithelial cells, to which HiLyte Fluor™ 555 labeled GI1.6 (7K) VLP had been added, with DAPI and anti-Zo-1 antibody. The left indicates a view obtained by overlapping a DAPI-stained image, an image stained with an anti-Zo-1 antibody, and a 7K VPL fluorescence image; the right indicates a 7K VPL fluorescence image. The scale bar indicates 10 μm. The arrow indicates VLP, and the arrowhead indicates a nucleus.

As shown in FIG. 10, it could be confirmed that GII.6 (7K) VLP does not only bind to human epithelial cells, but it also invades into the cytoplasm thereof (the arrows shown in FIG. 10 indicate the fluorescence of VLP).

From the results described in 3-2-1 and 3-2-2 above, it was confirmed that the nanoantibody according to the embodiment of the present invention effectively inhibits invasion of norovirus VLP into monolayered human intestinal epithelial cells.

4. Studies Regarding Effect of Nanoantibody to Inhibit Norovirus Infection

Human norovirus (HuNoV) was furnished from Osaka Institute of Public Health (GII.3 (16-50 strain), GII.4 (17-53 strain), and GII.17 (16-421 strain)).

Moreover, monolayered intestinal epithelial cells derived from iPS cells (TkDN4-M strain; Takayama et al., J. Exp. Med., 207:2817-2830 2010) were prepared from organoids that had been furnished from Dr. Shintaro SATO, Research Institute for Microbial Diseases, Osaka University. Specifically, cells were recovered from human iPS cell-derived organoids, which were maintained and sub-cultured according to the method of Takahashi et al. (Stem cell. Reports 10: 314-328, 2018), and the recovered cells were then seeded on a 96-well cell culture plate in an amount of $2\times10^4$ cells/well. Then, the cells were cultured according to the method of Takahashi et al. (EBioMedicine 23: 43-45, 2017) for 5 days, so as to prepare monolayered epithelial cells. For 48 hours before infection with the virus, the cells used for GII.3 infection were cultured under conditions with addition of 0.03% swine bile, whereas the cells used for GII.4 and GII.17 infection were cultured under conditions without addition of swine bile.

On the day of infection, HuNoV, the viral genome copy number of which had already been calculated, was mixed in an amount of $5\times10^6$ copies/well with the nanoantibody (5 μg/well) (KVP-7B8, KVP-7C6, KTP-7F10, and KVP-12B8), and the thus obtained mixture was then pre-incubated at 37° C. for 2 hours. After completion of the pre-incubation, only the virus, or a mixed solution of the virus and the nanoantibody, was added to iPS cell-derived monolayered intestinal epithelial cells, so that the cells were infected therewith at 37° C. for 3 hours. Three hours after the infection, the virus solutions were removed from all of the wells, and the wells were then washed twice. Thereafter, 100 μl of a medium was added to each well, and the added medium was then recovered as a 3 hpi sample (i.e., the sample 3 hours after the infection). After the recovery of the 3 hpi sample, 100 μl of a new medium was added to the well, and it was continuously cultured until 72 hours after the infection. Seventy-two hours later, the supernatant was recovered from each well, and it was used as a 72 hpi sample (i.e., the sample 72 hours after the infection).

From the 3 hpi and 72 hpi samples, RNAs were extracted, and the viral copy number of each sample was then calculated according to real-time PCR based on the official analytical method (4× TaqMan Fast Virus 1-Step Master Mix/life technologies #4444434).

Figure 11:
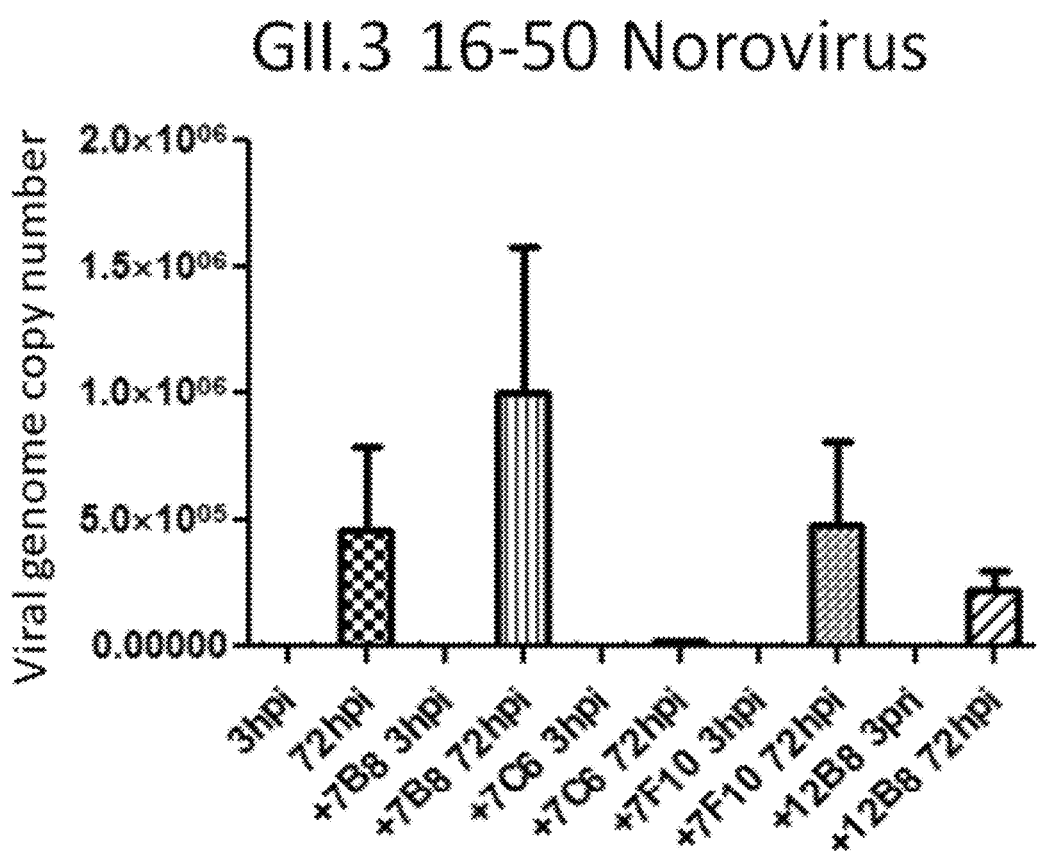
FIG. 11 shows the influence of the nanoantibodies (KVP-7B8, KVP-7C6, KVP-7F10, and KVP-12B8) on infection of intestinal epithelial cells with HuNoV GII.3 (16-50 strain). The virus was mixed with each nanoantibody, followed by pre-incubation, and the mixture was then added to the intestinal epithelial cell layer, so that the cells were infected with the virus. Three hours after viral infection (3 hpi) and 72 hours after viral infection (72 hpi), the viral copy number in the medium was measured.

FIG. 11 shows the influence of the nanoantibodies according to the present invention on infection of human intestinal epithelial cells with GII.3 (16-50 strain). When GII.3 was treated with KVP-7C6 and KVP-12B8, the viral copy number in the 72 hpi samples was significantly reduced. Accordingly, it was found that KVP-7C 6 and KVP-12B8 do not only inhibit the binding of HuNoV to intestinal epithelial cells but also inhibit the infection.

Figure 12:
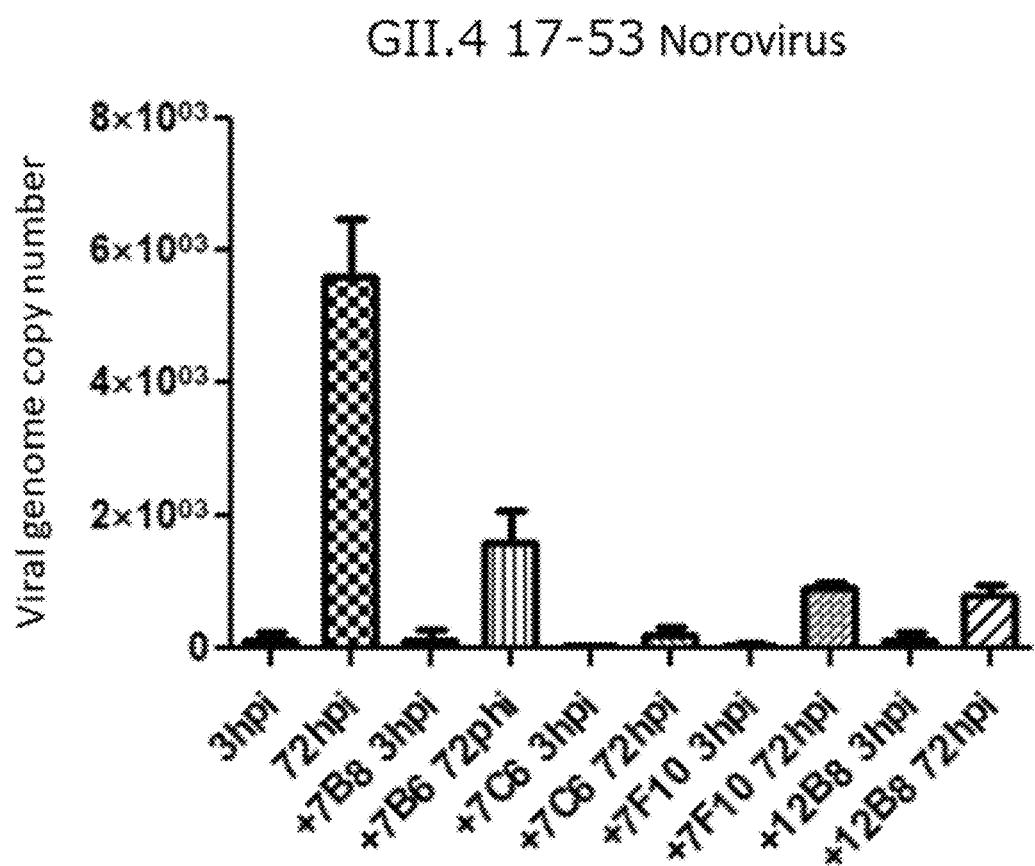
FIG. 12 shows the influence of the nanoantibodies (KVP-7B8, KVP-7C6, KVP-7F10, and KVP-12B8) on infection of intestinal epithelial cells with HuNoV GII.4 (17-53 strain). The virus was mixed with each nanoantibody, followed by pre-incubation, and the mixture was then added to intestinal epithelial cell layer, so that the cells were infected with the virus. Three hours after viral infection (3 hpi) and 72 hours after viral infection (72 hpi), the viral copy number in the medium was measured.

FIG. 12 shows the influence of the nanoantibodies according to the present invention on infection of human intestinal epithelial cells with GII.4 (17-53 strain). When GII.4 was treated with KVP-7B8, KVP-7C6, KVP-7F10 and KVP- 12B8, the viral copy number in the 72 hpi samples was significantly reduced. Accordingly, it was found that KVP-7B8, KVP-7C6 and KVP-12B8 do not only inhibit the binding of HuNoV to intestinal epithelial cells but also inhibit the infection.

Figure 13:
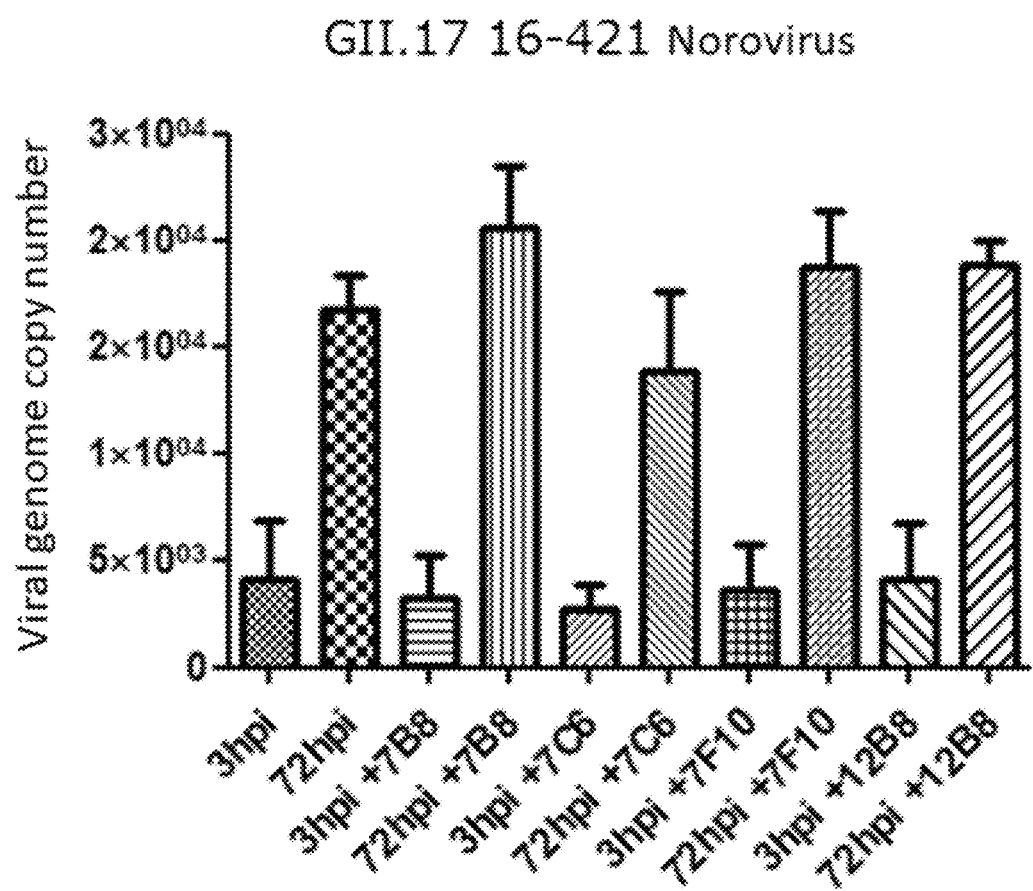
FIG. 13 shows the influence of the nanoantibodies (KVP-7B8, KVP-7C6, KVP-7F10, and KVP-12B8) on infection of intestinal epithelial cells with HuNoV GII.17 (16-421 strain). The virus was mixed with each nanoantibody, followed by pre-incubation, and the mixture was then added to intestinal epithelial cell layer, so that the cells were infected with the virus. Three hours after viral infection (3 hpi) and 72 hours after viral infection (72 hpi), the viral copy number in the medium was measured.

FIG. 13 shows the influence of the nanoantibodies according to the present invention on infection of human intestinal epithelial cells with GII.17 (16-421 strain). All of KVP-7B8, KVP-7C6, KVP-7F10 and KVP-12B8 did not exhibit effects on infection of the intestinal epithelial cells with GII.17.

INDUSTRIAL APPLICABILITY

The antibody according to the present invention has the effect of effectively inhibiting norovirus infection. Accordingly, it can be expected that the present invention will be utilized in the medical field.

The invention claimed is:

1. A nanoantibody, comprising:
the amino acid sequences of complementarity-determining regions 1 to 3 (CDR1, CDR2 and CDR3) of the following (A), (B), (C) or (D):
(A) CDR1 comprising the amino acid sequence as set forth in SEQ ID NO: 17,
CDR2 comprising the amino acid sequence as set forth in SEQ ID NO: 18, and
CDR3 comprising the amino acid sequence as set forth in SEQ ID NO: 19;
(B) CDR1 comprising the amino acid sequence as set forth in SEQ ID NO: 20,
CDR2 comprising the amino acid sequence as set forth in SEQ ID NO: 21, and
CDR3 comprising the amino acid sequence as set forth in SEQ ID NO: 22;
(C) CDR1 comprising the amino acid sequence as set forth in SEQ ID NO: 23,
CDR2 comprising the amino acid sequence as set forth in SEQ ID NO: 24, and
CDR3 comprising the amino acid sequence as set forth in SEQ ID NO: 25; and
(D) CDR1 comprising the amino acid sequence as set forth in SEQ ID NO: 26,
CDR2 comprising the amino acid sequence as set forth in SEQ ID NO: 27, and
CDR3 comprising the amino acid sequence as set forth in SEQ ID NO: 28,
wherein the nanoantibody inhibits infection of intestinal cells with HuNoV GII.4.

2. A pharmaceutical composition comprising the nanoantibody according to claim 1.

3. The pharmaceutical composition according to claim 2, wherein a therapeutic or preventive target of the pharmaceutical composition is norovirus infection.

4. A heavy-chain antibody comprising the nanoantibody according to claim 1.

5. A pharmaceutical composition comprising the heavy-chain antibody according to claim 4.

6. The pharmaceutical composition according to claim 5, wherein a therapeutic or preventive target of the pharmaceutical composition is norovirus infection.

7. A nanoantibody multimer, in which a plurality of the nanoantibodies according to claim 1 are connected with one another.

8. A pharmaceutical composition comprising the nanoantibody multimer according to claim 7.

9. The pharmaceutical composition according to claim 8, wherein a therapeutic or preventive target of the pharmaceutical composition is norovirus infection.

10. A nanoantibody multimer, in which one or a plurality of the nanoantibodies according to claim 1 are connected with one or a plurality of nanoantibodies each having antigen specificity that is different from the aforementioned nanoantibodies.

11. A pharmaceutical composition comprising the nanoantibody multimer according to claim 10.

12. The pharmaceutical composition according to claim 11, wherein a therapeutic or preventive target of the pharmaceutical composition is norovirus infection.

13. A nucleic acid encoding the nanoantibody according to claim 1.

14. A vector comprising the nucleic acid according to claim 13.

15. A cell, into which the vector according to claim 14 is introduced.

16. A transgenic rice plant, into which the nucleic acid according to claim 13 is introduced and the nanoantibody is expressed in rice grains thereof.

17. A rice grain harvested from the transgenic rice plant according to claim 16.

18. A nanoantibody comprising a polypeptide described in the following (a), (b), or (c):
    (a) a polypeptide consisting of the amino acid sequence as set forth in SEQ ID NO: 1, SEQ ID NO: 5, SEQ ID NO: 9, or SEQ ID NO: 13;
    (b) a polypeptide consisting of an amino acid sequence comprising a substitution, deletion, insertion and/or addition of one or several amino acids with respect to the amino acid sequence as set forth in SEQ ID NO: 1, SEQ ID NO: 5, SEQ ID NO: 9, or SEQ ID NO: 13; and
    (c) a polypeptide consisting of an amino acid sequence having a sequence identity of 80% or more to the amino acid sequence as set forth in SEQ ID NO: 1, SEQ ID NO: 5, SEQ ID NO: 9, or SEQ ID NO: 13, wherein the nanoantibody inhibits infection of intestinal cells with HuNoV GII.4, and
wherein the nanoantibody comprises the amino acid sequences of complementarity-determining regions 1 to 3 (CDR1, CDR2 and CDR3) of the following (A), (B), (C) or (D):
(A) CDR1 comprising the amino acid sequence as set forth in SEQ ID NO: 17,
    CDR2 comprising the amino acid sequence as set forth in SEQ ID NO: 18, and
    CDR3 comprising the amino acid sequence as set forth in SEQ ID NO: 19;
(B) CDR1 comprising the amino acid sequence as set forth in SEQ ID NO: 20,
    CDR2 comprising the amino acid sequence as set forth in SEQ ID NO: 21, and
    CDR3 comprising the amino acid sequence as set forth in SEQ ID NO: 22;
(C) CDR1 comprising the amino acid sequence as set forth in SEQ ID NO: 23,
    CDR2 comprising the amino acid sequence as set forth in SEQ ID NO: 24, and
    CDR3 comprising the amino acid sequence as set forth in SEQ ID NO: 25; and
(D) CDR1 comprising the amino acid sequence as set forth in SEQ ID NO: 26,
    CDR2 comprising the amino acid sequence as set forth in SEQ ID NO: 27, and
    CDR3 comprising the amino acid sequence as set forth in SEQ ID NO: 28.

19. A nucleic acid as set forth in SEQ ID NO: 2, SEQ ID NO: 6, SEQ ID NO: 10, or SEQ ID NO: 14.

20. A vector comprising the nucleic acid according to claim 19.

21. A cell, into which the vector according to claim 20 is introduced.

22. A transgenic rice plant, into which the nucleic acid according to claim 19 is introduced and the nanoantibody is expressed in rice grains thereof.

23. A rice grain harvested from the transgenic rice plant according to claim 22.

* * * * *